US006933154B2

(12) United States Patent
Schomacker et al.

(10) Patent No.: US 6,933,154 B2
(45) Date of Patent: Aug. 23, 2005

(54) OPTIMAL WINDOWS FOR OBTAINING OPTICAL DATA FOR CHARACTERIZATION OF TISSUE SAMPLES

(75) Inventors: Kevin T. Schomacker, Maynard, MA (US); Alex Zelenchuk, Stoughton, MA (US); Ross Flewelling, Chelmsford, MA (US); Howard Kaufman, Newton, MA (US)

(73) Assignee: MediSpectra, Inc., Lexington, MA (US)

( * ) Notice: Subject to any disclaimer, the term of this patent is extended or adjusted under 35 U.S.C. 154(b) by 227 days.

(21) Appl. No.: 10/295,794

(22) Filed: Nov. 15, 2002

(65) Prior Publication Data
US 2004/0023406 A1 Feb. 5, 2004

Related U.S. Application Data

(60) Provisional application No. 60/394,696, filed on Jul. 9, 2002.

(51) Int. Cl.[7] ............................................. G01N 31/00
(52) U.S. Cl. ....................... 436/164; 436/166; 436/171; 436/172; 436/174; 435/29; 435/808
(58) Field of Search ................... 424/9.8, 9.1; 514/557; 600/407, 408, 310; 436/172

(56) References Cited

U.S. PATENT DOCUMENTS

| | | | |
|---|---|---|---|
| 3,013,467 A | 12/1961 | Minsky | 88/14 |
| 3,632,865 A | 1/1972 | Haskell et al. | 178/6 |
| 3,809,072 A | 5/1974 | Ersek et al. | 128/23 |
| 3,890,462 A | 6/1975 | Limb et al. | 178/6.8 |
| 3,963,019 A | 6/1976 | Quandt et al. | 128/2 |
| D242,393 S | 11/1976 | Bauman | D83/12 R |
| D242,396 S | 11/1976 | Bauman | D83/12 R |
| D242,397 S | 11/1976 | Bauman | D83/12 R |
| D242,398 S | 11/1976 | Bauman | D83/12 R |
| 4,017,192 A | 4/1977 | Rosenthal et al. | 356/201 |

(Continued)

FOREIGN PATENT DOCUMENTS

| | | | |
|---|---|---|---|
| EP | 0 135 134 | 3/1985 | |
| EP | 0 280 418 | 8/1988 | |
| EP | 0 335 725 | 10/1989 | |
| EP | 0 444 689 A2 | 9/1991 | |
| EP | 0 474 264 | 3/1992 | |
| EP | 0 641 542 | 3/1995 | |
| EP | 0 689 045 A1 | 12/1995 | |
| EP | 0 737 849 A2 | 10/1996 | |
| JP | 08-280602 | 10/1996 | ............ A61B/1/00 |
| SU | 1 223 092 A | 4/1986 | |

(Continued)

OTHER PUBLICATIONS

Agrawal et al. (1999), "Fluorescence Spectroscopy of the Cervix: Influence of Acetic Acid, Cervical Mucus, and Vaginal Medications," *Lasers in Surgery and Medicine*, 25:237–249.

Althof et al. (1997), "A rapid and automatic image registration algorithm with subpixel accuracy," *IEEE Transactions on Medical Imaging*, 16(3):308–316.

Anderson (1994), "Confocal Laser Microscopes See A Wider Field of Application", *Laser Focus World*, pp. 83–86.

(Continued)

*Primary Examiner*—Jill Warden
*Assistant Examiner*—Sam P. Siefke
(74) *Attorney, Agent, or Firm*—Testa, Hurwitz & Thibeault, LLP

(57) ABSTRACT

The invention provides methods for determining a characteristic of a tissue sample, such as a state of health, using spectral data and/or images obtained within an optimal period of time following the application of a chemical agent to the tissue sample. The invention provides methods of determining such optimal windows of time. Similarly, the invention provides methods of determining other criteria for triggering the acquisition of an optical signal for classifying the state of health of a region of a tissue sample.

24 Claims, 17 Drawing Sheets

U.S. PATENT DOCUMENTS

| | | |
|---|---|---|
| 4,071,020 A | 1/1978 | Puglise et al. .................. 128/2 |
| 4,198,571 A | 4/1980 | Sheppard ..................... 250/571 |
| 4,218,703 A | 8/1980 | Netravali et al. ........... 358/136 |
| 4,254,421 A | 3/1981 | Kreutel, Jr. .................. 343/754 |
| 4,273,110 A | 6/1981 | Groux ............................ 128/6 |
| 4,357,075 A | 11/1982 | Hunter ....................... 350/294 |
| 4,397,557 A | 8/1983 | Herwig et al. .............. 356/342 |
| 4,515,165 A | 5/1985 | Carroll ....................... 128/664 |
| 4,549,229 A | 10/1985 | Nakano et al. ................. 360/8 |
| 4,558,462 A | 12/1985 | Horiba et al. ................. 382/42 |
| 4,641,352 A | 2/1987 | Fenster et al. .................. 382/6 |
| 4,646,722 A | 3/1987 | Silverstein et al. ............ 128/4 |
| 4,662,360 A | 5/1987 | O'Hara et al. ................. 128/9 |
| 4,733,063 A | 3/1988 | Kimura et al. .............. 250/201 |
| 4,741,326 A | 5/1988 | Sidall et al. .................... 128/4 |
| 4,753,530 A | 6/1988 | Knight et al. ................. 356/73 |
| 4,768,513 A | 9/1988 | Suzuki ........................ 128/634 |
| 4,800,571 A | 1/1989 | Konishi ......................... 375/10 |
| 4,844,617 A | 7/1989 | Kelderman et al. ......... 356/372 |
| 4,845,352 A | 7/1989 | Benschop ................... 250/201 |
| 4,852,955 A | 8/1989 | Doyle et al. ................. 350/1.2 |
| 4,877,033 A | 10/1989 | Seitz, Jr. ................ 128/660.05 |
| 4,878,485 A | 11/1989 | Adair ............................ 128/6 |
| 4,891,829 A | 1/1990 | Deckman et al. .............. 378/4 |
| 4,930,516 A | 6/1990 | Alfano et al. ............... 128/665 |
| 4,945,478 A | 7/1990 | Merickel et al. ........ 364/413.22 |
| 4,965,441 A | 10/1990 | Picard ..................... 250/201.3 |
| 4,972,258 A | 11/1990 | Wolf et al. .................... 358/93 |
| 4,974,580 A | 12/1990 | Anapliotis ..................... 128/4 |
| 4,979,498 A | 12/1990 | Oneda et al. ................... 128/6 |
| 4,997,242 A | 3/1991 | Amos ........................ 350/6.91 |
| 5,003,979 A | 4/1991 | Merickel et al. ........ 364/413.22 |
| 5,011,243 A | 4/1991 | Doyle et al. ................. 350/1.2 |
| 5,022,757 A | 6/1991 | Modell ........................ 356/318 |
| 5,028,802 A | 7/1991 | Webb et al. ................. 250/571 |
| 5,032,720 A | 7/1991 | White ......................... 250/236 |
| 5,034,613 A | 7/1991 | Denk et al. ............... 250/458.1 |
| 5,036,853 A | 8/1991 | Jeffcoat et al. .............. 128/634 |
| 5,042,494 A | 8/1991 | Alfano ........................ 128/665 |
| 5,048,946 A | 9/1991 | Sklar et al. .................. 351/206 |
| 5,054,926 A | 10/1991 | Dabbs et al. ................ 356/345 |
| 5,065,008 A | 11/1991 | Hakamata et al. .......... 250/216 |
| 5,071,246 A | 12/1991 | Blaha et al. ................. 351/221 |
| 5,074,306 A | 12/1991 | Green et al. ................. 128/664 |
| 5,083,220 A | 1/1992 | Hill ............................. 359/234 |
| 5,091,652 A | 2/1992 | Mathies et al. .......... 250/458.1 |
| 5,101,825 A | 4/1992 | Gravenstein et al. ....... 128/633 |
| 5,120,953 A | 6/1992 | Harris ...................... 250/227.2 |
| 5,122,653 A | 6/1992 | Ohki ........................... 250/216 |
| 5,132,526 A | 7/1992 | Iwasaki .................... 250/201.3 |
| 5,139,025 A | 8/1992 | Lewis et al. ................. 128/665 |
| 5,154,166 A | 10/1992 | Chikama ....................... 128/4 |
| 5,159,919 A | 11/1992 | Chikama ....................... 128/4 |
| 5,161,053 A | 11/1992 | Dabbs ........................ 359/384 |
| 5,162,641 A | 11/1992 | Fountain .................. 250/201.2 |
| 5,162,941 A | 11/1992 | Favro et al. ................. 359/386 |
| 5,168,157 A | 12/1992 | Kimura ..................... 250/201.3 |
| 5,192,980 A | 3/1993 | Dixon et al. ................ 356/326 |
| 5,193,525 A | 3/1993 | Silverstein et al. ............ 128/4 |
| RE34,214 E | 4/1993 | Carlsson et al. .............. 358/93 |
| 5,199,431 A | 4/1993 | Kittrell et al. .............. 128/634 |
| 5,201,318 A | 4/1993 | Rava et al. .................. 128/665 |
| 5,201,908 A | 4/1993 | Jones ............................ 128/4 |
| 5,203,328 A | 4/1993 | Samuels et al. ............. 128/633 |
| 5,225,671 A | 7/1993 | Fukuyama ................... 250/216 |
| 5,235,457 A | 8/1993 | Lichtman et al. ........... 359/368 |
| 5,237,984 A | 8/1993 | Williams, III et al. .......... 128/4 |
| 5,239,178 A | 8/1993 | Derndinger et al. ........ 250/234 |
| 5,248,876 A | 9/1993 | Kerstens et al. ............. 250/561 |
| 5,253,071 A | 10/1993 | MacKay .................... 358/222 |
| 5,257,617 A | 11/1993 | Takahashi ....................... 128/4 |
| 5,260,569 A | 11/1993 | Kimura ....................... 250/234 |
| 5,260,578 A | 11/1993 | Bliton et al. ............... 250/461.1 |
| 5,261,410 A | 11/1993 | Alfano et al. ............... 128/664 |
| 5,262,646 A | 11/1993 | Booker et al. .............. 250/341 |
| 5,274,240 A | 12/1993 | Mathies et al. .......... 250/458.1 |
| 5,284,149 A | 2/1994 | Dhadwal et al. ............ 128/665 |
| 5,286,964 A | 2/1994 | Fountain .................. 250/201.2 |
| 5,289,274 A | 2/1994 | Kondo ........................ 348/208 |
| 5,294,799 A | 3/1994 | Aslund et al. ............ 250/458.1 |
| 5,296,700 A | 3/1994 | Kumagai .................... 250/216 |
| 5,303,026 A | 4/1994 | Strobl et al. ................ 356/318 |
| 5,306,902 A | 4/1994 | Goodman ................. 250/201.3 |
| 5,313,567 A | 5/1994 | Civanlar et al. ............. 395/124 |
| 5,319,200 A | 6/1994 | Rosenthal et al. .......... 250/341 |
| 5,321,501 A | 6/1994 | Swanson et al. ............ 356/345 |
| 5,324,979 A | 6/1994 | Rosenthal ............... 250/504 R |
| 5,325,846 A | 7/1994 | Szabo ........................... 128/4 |
| 5,329,352 A | 7/1994 | Jacobsen .................... 356/301 |
| 5,337,734 A | 8/1994 | Saab ............................ 128/4 |
| 5,343,038 A | 8/1994 | Nishiwaki et al. .......... 250/234 |
| 5,345,306 A | 9/1994 | Ichimura et al. ............ 356/346 |
| 5,345,941 A | 9/1994 | Rava et al. .................. 128/665 |
| 5,349,961 A | 9/1994 | Stoddart et al. ............. 128/665 |
| 5,398,685 A | 3/1995 | Wilk et al. ................ 128/653.1 |
| 5,402,768 A | 4/1995 | Adair ............................ 128/4 |
| 5,406,939 A | 4/1995 | Bala ............................. 128/4 |
| 5,413,092 A | 5/1995 | Williams, III et al. .......... 128/4 |
| 5,413,108 A | 5/1995 | Alfano ........................ 128/665 |
| 5,415,157 A | 5/1995 | Welcome ..................... 128/4 |
| 5,418,797 A | 5/1995 | Bashkansky et al. ........... 372/3 |
| 5,419,311 A | 5/1995 | Yabe et al. .................... 128/4 |
| 5,419,323 A | 5/1995 | Kittrell et al. .............. 128/653 |
| 5,421,337 A | 6/1995 | Richards-Kortum et al. .......................... 128/665 |
| 5,421,339 A | 6/1995 | Ramanujam et al. ....... 128/665 |
| 5,424,543 A | 6/1995 | Dombrowski et al. ...... 250/330 |
| 5,450,857 A | 9/1995 | Garfield et al. ............. 128/778 |
| 5,451,931 A | 9/1995 | Miller et al. ................ 340/630 |
| 5,458,132 A | 10/1995 | Yabe et al. .................... 128/4 |
| 5,458,133 A | 10/1995 | Yabe et al. .................. 600/121 |
| 5,467,767 A | 11/1995 | Alfano et al. ............... 128/665 |
| 5,469,853 A | 11/1995 | Law et al. .............. 128/662.06 |
| 5,477,382 A | 12/1995 | Pernick ....................... 359/559 |
| 5,480,775 A | 1/1996 | Ito et al. ....................... 435/7.2 |
| 5,493,444 A | 2/1996 | Khoury et al. .............. 359/559 |
| 5,496,259 A | 3/1996 | Perkins ........................ 600/124 |
| 5,507,295 A | 4/1996 | Skidmore .................... 600/121 |
| 5,516,010 A | 5/1996 | O'Hara et al. ............... 600/122 |
| 5,519,545 A | 5/1996 | Kawahara ..................... 360/46 |
| 5,529,235 A | 6/1996 | Bolarski et al. .......... 227/175.1 |
| 5,536,236 A | 7/1996 | Yabe et al. .................. 600/125 |
| 5,545,121 A | 8/1996 | Yabe et al. .................. 600/121 |
| 5,551,945 A | 9/1996 | Yabe et al. .................. 600/122 |
| 5,556,367 A | 9/1996 | Yabe et al. .................. 600/124 |
| 5,562,100 A | 10/1996 | Kittrell et al. ............... 128/665 |
| 5,579,773 A | 12/1996 | Vo-Dinh et al. ............. 128/665 |
| 5,582,168 A | 12/1996 | Samuels et al. ............. 128/633 |
| 5,587,832 A | 12/1996 | Krause ........................ 359/385 |
| 5,596,992 A | 1/1997 | Haaland et al. ............. 128/664 |
| 5,599,717 A | 2/1997 | Vo-Dinh ....................... 436/63 |
| 5,609,560 A | 3/1997 | Ichikawa et al. ............ 600/101 |
| 5,612,540 A | 3/1997 | Richards-Korum et al. .......................... 250/461.2 |
| 5,623,932 A | 4/1997 | Ramanujam et al. ....... 128/665 |
| 5,643,175 A | 7/1997 | Adair .......................... 600/133 |
| 5,647,368 A | 7/1997 | Zeng et al. .................. 128/665 |
| 5,662,588 A | 9/1997 | Lida ............................ 600/121 |
| 5,685,822 A | 11/1997 | Harhen ....................... 600/125 |

| | | | | | |
|---|---|---|---|---|---|
| 5,690,106 A | 11/1997 | Bani-Hashemi et al. .. 128/653.1 | D453,962 S | 2/2002 | Morrell et al. ............. D24/138 |
| 5,693,043 A | 12/1997 | Kittrell et al. ................ 606/15 | D453,963 S | 2/2002 | Morrell et al. ............. D24/138 |
| 5,695,448 A | 12/1997 | Kimura et al. ............. 600/121 | D453,964 S | 2/2002 | Morrell et al. ............. D24/138 |
| 5,697,373 A | 12/1997 | Richards-Kortum et al. ........................ 128/664 | 6,377,842 B1 | 4/2002 | Pogue et al. ................ 600/478 |
| | | | 6,385,484 B2 | 5/2002 | Nordstrom et al. ......... 600/476 |
| 5,699,795 A | 12/1997 | Richards-Kortum ....... 128/634 | 6,411,835 B1 | 6/2002 | Modell et al. .............. 600/407 |
| 5,704,892 A | 1/1998 | Adair ......................... 600/121 | 6,411,838 B1 | 6/2002 | Nordstrom et al. ......... 600/476 |
| 5,707,343 A | 1/1998 | O'Hara et al. .............. 600/121 | D460,821 S | 7/2002 | Morrell et al. ............. D24/138 |
| 5,713,364 A | 2/1998 | DeBaryshe et al. ......... 128/664 | 6,421,553 B1 | 7/2002 | Costa et al. ................ 600/476 |
| 5,717,209 A | 2/1998 | Bigman et al. ........ 250/339.12 | 6,427,082 B1 | 7/2002 | Nordstrom et al. ......... 600/476 |
| 5,730,701 A | 3/1998 | Furukawa et al. .......... 600/127 | 6,571,118 B1 | 5/2003 | Utzinger et al. ............ 600/476 |
| 5,733,244 A | 3/1998 | Yasui et al. ................. 600/127 | 6,574,502 B2 | 6/2003 | Hayashi ..................... 600/476 |
| 5,735,276 A | 4/1998 | Lemelson et al. .......... 128/653 | 6,760,613 B2 | 7/2004 | Nordstrom et al. ......... 600/476 |
| 5,746,695 A | 5/1998 | Yasui et al. ................. 600/127 | 2002/0007122 A1 | 1/2002 | Kaufman et al. ........... 600/476 |
| 5,768,333 A | 6/1998 | Abdel-Mottaleb ........... 378/37 | 2002/0007123 A1 | 1/2002 | Balas et al. ................ 600/476 |
| 5,769,792 A | 6/1998 | Palcic et al. ................ 600/477 | 2002/0107668 A1 | 8/2002 | Costa et al. ................ 702/189 |
| 5,773,835 A | 6/1998 | Sinofsky et al. .......... 250/462.1 | 2002/0127735 A1 | 9/2002 | Kaufman et al. ........... 600/436 |
| 5,791,346 A | 8/1998 | Craine et al. ............... 128/653 | 2002/0177777 A1 | 11/2002 | Nordstrom et al. ......... 600/475 |
| 5,795,632 A | 8/1998 | Buchalter .................. 428/35.2 | 2002/0183626 A1 | 12/2002 | Nordstrom et al. ......... 600/476 |
| 5,800,350 A | 9/1998 | Coppleson et al. ......... 600/372 | 2003/0095721 A1 | 5/2003 | Clune et al. ................ 382/294 |
| 5,807,248 A | 9/1998 | Mills .......................... 600/322 | 2003/0144585 A1 | 7/2003 | Kaufman et al. ........... 600/407 |
| 5,813,987 A | 9/1998 | Modell et al. .............. 600/473 | 2004/0007674 A1 | 1/2004 | Schomacker et al. .... 250/458.1 |
| 5,817,015 A | 10/1998 | Adair ......................... 600/121 | 2004/0010187 A1 | 1/2004 | Schomacker et al. ....... 600/317 |
| 5,830,146 A | 11/1998 | Skladnev et al. ........... 600/478 | 2004/0010195 A1 | 1/2004 | Zelenchuk .................. 600/476 |
| 5,833,617 A | 11/1998 | Hayashi ..................... 600/476 | | | |
| 5,840,035 A | 11/1998 | Heusmann et al. ........... 600/47 | | | |
| 5,842,995 A | 12/1998 | Mahadevan-Jansen et al. ........................ 600/473 | | | |

FOREIGN PATENT DOCUMENTS

| | | | |
|---|---|---|---|
| WO | WO 92/19148 | 11/1992 | |
| WO | WO 93/14688 | 8/1993 | |
| WO | WO 94/26168 | 11/1994 | |
| WO | WO 95/00067 | 1/1995 | ............ A61B/1/22 |
| WO | WO 95/04385 | 2/1995 | |
| WO | WO 97/05473 | 2/1997 | |
| WO | WO 98/30889 | 2/1997 | |
| WO | WO 97/48331 | 12/1997 | |
| WO | WO 98/05253 | 2/1998 | |
| WO | WO 98/24369 | 6/1998 | |
| WO | WO 98/41176 | 9/1998 | |
| WO | WO 99/18847 | 4/1999 | |
| WO | WO 99/20313 | 4/1999 | |
| WO | WO 99/20314 | 4/1999 | |
| WO | WO 99/47041 | 9/1999 | |
| WO | WO 99/57507 | 11/1999 | |
| WO | WO 99/57529 | 11/1999 | |
| WO | WO 00/15101 | 3/2000 | |
| WO | WO 00/41615 | 7/2000 | |
| WO | WO 00/57361 | 9/2000 | |
| WO | WO 00/59366 | 10/2000 | |
| WO | WO 00/74556 | 12/2000 | |

Continuing US patent references:

| | | |
|---|---|---|
| 5,855,551 A | 1/1999 | Sklandnev et al. ......... 600/372 |
| 5,860,913 A | 1/1999 | Yamaya et al. ............. 600/127 |
| 5,863,287 A | 1/1999 | Segawa ...................... 600/121 |
| 5,865,726 A | 2/1999 | Katsurada et al. .......... 600/127 |
| 5,876,329 A | 3/1999 | Harhen ....................... 600/125 |
| 5,920,399 A | 7/1999 | Sandison et al. ........... 356/418 |
| 5,921,926 A | 7/1999 | Rolland et al. ............. 600/407 |
| 5,929,985 A | 7/1999 | Sandison et al. ........... 365/318 |
| 5,931,779 A | 8/1999 | Arakaki et al. ............. 600/310 |
| 5,938,617 A | 8/1999 | Vo-Dinh ..................... 600/476 |
| 5,941,834 A | 8/1999 | Skladnev et al. ........... 600/587 |
| 5,983,125 A | 11/1999 | Alfano et al. ............... 600/473 |
| 5,989,184 A | 11/1999 | Blair .......................... 600/167 |
| 5,991,653 A | 11/1999 | Richards-Kortum et al. ........................ 660/475 |
| 5,995,645 A | 11/1999 | Soenksen et al. ........... 382/133 |
| 6,021,344 A | 2/2000 | Lui et al. .................... 600/476 |
| 6,058,322 A | 5/2000 | Nishikawa et al. ......... 600/408 |
| 6,069,689 A | 5/2000 | Zeng et al. ................. 356/773 |
| 6,083,487 A * | 7/2000 | Biel ............................ 424/9.6 |
| 6,091,985 A | 7/2000 | Alfano et al. ............... 600/476 |
| 6,095,982 A | 8/2000 | Richards-Kortum et al. ........................ 600/476 |
| 6,096,065 A | 8/2000 | Crowley ....................... 607/88 |
| 6,099,464 A | 8/2000 | Shimizu et al. ............. 600/104 |
| 6,104,945 A | 8/2000 | Modell et al. .............. 600/473 |
| 6,119,031 A | 9/2000 | Crowley ..................... 600/407 |
| 6,124,597 A | 9/2000 | Shehada et al. .......... 250/461.2 |
| 6,146,897 A | 11/2000 | Cohenford et al. ........... 436/63 |
| 6,169,817 B1 | 1/2001 | Parker et al. ................ 382/131 |
| 6,187,289 B1 * | 2/2001 | Richards-Kortum et al. .. 424/9.8 |
| 6,208,887 B1 | 3/2001 | Clarke et al. ............... 600/476 |
| 6,241,662 B1 | 6/2001 | Richards-Kortum et al. ........................ 600/310 |
| 6,243,601 B1 | 6/2001 | Wist ........................... 600/473 |
| 6,246,471 B1 | 6/2001 | Jung et al. .................... 356/73 |
| 6,246,479 B1 | 6/2001 | Jung et al. .................. 356/419 |
| 6,258,576 B1 | 7/2001 | Richards-Kortum et al. ........................ 435/172 |
| 6,285,639 B1 | 9/2001 | Maenza et al. .......... 369/47.28 |
| 6,312,385 B1 | 11/2001 | Mo et al. .................... 600/443 |
| 6,317,617 B1 | 11/2001 | Gilhuijs et al. ............. 600/408 |
| D453,832 S | 2/2002 | Morrell et al. ............. D24/138 |

OTHER PUBLICATIONS

Aström et al. (1999), "Motion estimation in image sequences using the deformation of apparent contours," *IEEE Transactions on Pattern Analysis and Machine Intelligence*, 21(2):114–127.

Balakrishnama et al, "Linear Discriminant Analysis—A Brief Tutorial," *Institute for Signal and Information Processing Department of Electrical and Computer Engineering*, 8 pages.

Balas (1997), "An Imaging Colorimeter for Noncontact Tissue Color Mapping," *IEEE Transactions on Biomedical Engineering*, 44(6):468–474.

Balas (2001), "A Novel Optical Imaging Method for the Early Detection, Quantitative Grading, and Mapping of Cancerous and Precancerous Lesions of Cervix," *IEEE Transactions on Biomedical Engineering*, 48(1):96–104.

Balas et al. (1997), "A modular diffuse reflection and fluorescence emission imaging colorimeter for the in–vivo study of parameters related with the phototoxic effect in PDT," *SPIE*, 3191:50–57.

Balas et al. (1998), "In Vivo Assessment of Acetic Acid–Cervical Tissue Interaction Using Quantitative Imaging of Back–Scattered Light: Its Potential Use for the In Vivo Cervical Cancer Detection Grading and Mapping," Part of EUROPTO Conference on Optical Biopsy, Stockholm, Sweden, *SPIE*, vol. 3568:31–37.

Balas et al. (1999), "In Vivo Detection and Staging of Epithelial Dysplasias and Malignancies Based on the Quantitative Assessment of Acetic Acid–Tissue Interaction Kinetics," *Journal of Photochemistry and Photobiology B: Biology*, 53:153–157.

Bessey et al. (1949), "The Fluorometric measurement of the nucleotides of riboflavin and their concentration in tissues," *J. Biol.–Chem.*; 180:755–769.

Bors et al. (1998), "Optical flow estimation and moving object segmentation based on median radial basis function network," *IEEE Transactions on Image Processing*, 7(5):693–702.

Bouthemy et al. (1999), "A unified approach to shot change detection and camera motion characterization," *IEEE Transactions on Circuits and Systems for Video Technology*, 9(7):1030–1044.

Braichotte et al. (1995), "Clinical Pharmacokinetic Studies of Photofrin by Fluorescence Spectroscopy in the Oral Cavity, the Esophagus, and the Bronchi," *Cancer* 75(11):2760–2778.

Brown (1990), "Chemometrics," *Anal. Chem.*, 62:84R–101R.

Camus et al. (1997), "Real–time quantized optical flow," *Real–Time Imaging*, 3:71–86.

Caplier et al. (1998), "Real–time implementation of a MRF–based motion detection algorithm," *Real–Time Imaging*, 4:41–54.

Contini et al. (1989), "Colposcopy and Computer Graphics: a New Method?" *Amer. J. Obstet. Gynecol.*, 160(3):535–538.

Craine et al. (1993), "Digital Imaging Colposcopy: basic concepts and applications," *Amer. J. Obstet. Gynecol.*, 82(5):869–873.

Craine et al. (1998), "Digital imaging colposcopy: Corrected area measurements using shape–from–shading." *IEEE Transactions on Medical Imaging*, 17(6):1003–1010.

Crisp et al. (1990), "The Computerized Digital Imaging Colposcope: Future Directions," *Amer. J. Obstet. Gynecol.*, 162(6):1491–1497.

Cronjé et al. (1997), "Effects of Dilute Acetic Acid on the Cervical Smear," *Acta. Cytol.*, 41:1091–1094.

Davidovits et al. (1971), "Scanning Laser Microscope for Biological Investigations", *Applied Optics*, 10(7):1615–1619.

Dickman et al. (2001), "Identification of Cervical Neoplasia Using a Simulation of Human Vision," *Journal of Lower Genital Tract Disease*, 5(3):144–152.

Drezek et al. (1999), "Light scattering from cells: finite–difference time–domain simulations and goniometrics measurements," *Applied Optics* 38(16):3651–3661.

Drezek et al. (2000), "Laser Scanning Confocal Microscopy of Cervical Tissue Before and After Application of Acetic Acid," *Am. J. Obstet. Gynecol.*, 182(5):1135–1139.

Dumontier et al. (1999), "Real–time DSP implementation for MRF–based video motion detection," *IEEE Transactions on Image Processing*, 8(10):1341–1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence*, 18(9):927–932.

Edebriri, A.A. (1990), "The relative significance of colposcopic discriptive appearances in the dianosis of cervical intraepithelial neoplasia," *Int. J. Gynecol. Obstet.*, 33:23–29.

Eisner et al. (1987), "Use of Cross–Correlation Function to Detect Patient Motion During Spectral Imaging," *Journal of Nuclear Medicine*, 28(1):97–101.

Ferris et al. (1998), "Colposcopy Quality Control: Establishing Colposcopy Criterion Standards for the NCI ALTS Trial Using Cervigrams," *J. Lower Genital Tract Disease*, 2(4):195–203.

Fleet et al. (1995), "Recursive Filters for Optical Flow," *IEEE Transactions on Pattern Analysis and Machine Intelligence*, 17(1):61–67.

Gao et al. (1998), "A work minimization approach to image morphing," *The Visual Computer*, 14:390–400.

Gauch (1999), "Image Segmentation and Analysis Via Multiscale Gradient Watershed Hierarchies," *IEEE Transactions on Image Processing*, 8(1):69–79.

Hall et al. (1992), "Near–Infrared Spectrophotometry: A New Dimension in Clinical Chemistry", *Clin. Chem.* 38(9):1623–1631.

Haralick (1984), "Digital Step Edges from Zero Crossing of Second Directional Derivatives," *IEEE Transactions on Pattern Analysis and Machine Intelligence*, 6(1):58–68.

Haris et al. (1998), "Hybrid Image Segmentation Using Watersheds and Fast Region Merging," *IEEE Transactions on Image Processing*, 7(12):1684–1699.

Helmerhorst et al. (1987), "The accuracy of colposcopically directed biopsy in diagnosis of CIN 2/3." *Eur. J. Obstet. Gyn. Reprod. Biol.*, 24, 221–229.

Horn et al. (1981), "Determining Optical Flow," *Artificial Intelligence*, 17(1–3):185–203.

Horn et al. (1993), "Determing Optical Flow": a retrospective, *Artificial Intelligence*, 59:81–87.

Huang et al. (1979), "A fast two–dimensional median filtering algorithm," *IEEE Transactions on Acoustics, Speech, and Signal Processing*, 27(1):13–18.

Jackway (1996), "Gradient Watersheds in Morphological Scale–Space," *IEEE Transactions on Image Processing*, 5(6):913–921.

Ji et al. (2000), "Texture Analysis for Classification of Cervix Lesions," *IEEE Transactions on Medical Imaging*, 19(11):1144–1149.

Kierkegaard et al. (1995), "Association between Colposcopic Findings and Histology in Cervical Lesions: The Significance of the Size of the Lesion" *Gynecologic Oncology*, 57:66–71.

Koester (1980), "Scanning Mirror Microscope with Optical Sectioning Characteristics: Applications in Ophthalmology", *Applied Optics*, 19(11):1749–1757.

Koester, "Comparison of Optical Sectioning Methods: The Scanning Slit Confocal Microscope", *Confocal Microscope Handbook*, pp. 189–194.

Kumar et al. (1996), "Optical Flow: A Curve Evolution Approach," *IEEE Transactions on Image Processing*, 5(4):598–610.

Linde et al. (1980), An algorithm for vector quantizer design,: *IEEE Transactions on Communications*, 28(1):84–95.

MacAulay et al. (2002), "Variation of fluorescence spectroscopy during the menstrual cycle," *Optics Express*, 10(12):493–504.

MacLean A.B. (1999), "What is Acetowhite Epithelium," *Abstract Book: 10th World Congress of Cervical Pathology and Colposcopy, Nov. 7–11*, Buenos Aires, Argentina 41.

Marzetta et al. (1999), "A surprising radon transform result and its application to motion detection," *IEEE Transactions on Image Processing*, 8(8):1039–1049.

Miike et al. (1999), "Motion enhancement for preprocessing of optical flow and scientific visualization," *Pattern Recognition Letters*, 20:451–461.

Mikhail et al. (1995), "Computerized colposcopy and conservative management of cervical intraepithelial neoplasia in pregnancy," *Acta Obstet. Gynecol. Scand.*, 74:376–378.

Milanfar (1999), "Two–dimensional matched filtering for motion estimation," *IEEE Transactions on Image Processing*, 8(3):438–444.

Mitchell et al. (1998), "Colposcopy for the diagnosis of squamous intraepithelial lesions: a meta–analysis," *Obstet. Gynecol.*, 91(4):626–631.

Mycek et al. (1998), "Colonic polyp differentiation using time–resolved autofluorescence spectroscopy," *Gastrointestinal Endoscopy*, 48(4):390–394.

Nanda et al. (2000), "Accuracy of the Papanicolaou test in screening for and follow–up of cervical cytologic abnormalities: a systematic review," *Ann Intern Med.*, 132(10):810–819.

Nesi et al. (1998), "RETIMAC REalTIme Motion Analysis Chip," *IEEE Transactions on Circuits and Systems–II: Analog and Digital Signal Processing*, 45(3):361–375.

Noumeir et al. (1996), "Detection of Motion During Tomographic Acquisition by an Optical Flow Algorithm," *Computers and Biomedical Research*, 29(1):1–15.

O'Sullivan et al. (1994), "Interobserver variation in the diagnosis and grading of dyskaryosis in cervical smears: specialist cytopathologists compared with non–specialists," *J. Clin. Pathol.*, 47(6):515–518.

Ogura et al. (1995), "A cost effective motion estimation processor LSI using a simple and efficient algorithm," *IEEE Transactions on Consumer Electronics*, 41(3):690–698.

Okatani et al. (1997), "Shape reconstruction from an endoscope image by shape from shading technique for a point light source at the projection center," *Computer Vision and Image Understanding*, 66(2):119–131.

Pan et al. (1998), "Correlation–feedback Technique in Optical Flow Determination," *IEEE Transactions on Image Processing*, 7(7):1061–1067.

Perona et al. (1990), "Scale–space and edge detection using anisotropic diffusion," *IEEE Transactions on Pattern Analysis and Machine Intelligence*, 12(7):629–639.

Pogue et al. (2001), "Analysis of Acetic Acid–Induced Whitening of High–Grade Squamous Intraepithelial Lesions," *Journal of Biomedical Optics*, 6(4):397–403.

Radjadhyaksha et al. (2000), "Confocal microscopy of excised human skin using acetic acid and crossed polarization: rapid detection of non–melanoma skin cancers," *Proceedings of SPIE*, 3907:84–88.

Rakshit et al. (1997), "Computation of Optical Flow Using Basis Functions," *IEEE Transactions on Image Processing*, 6(9):1246–1254.

Ramanujam et al. (1994) "In vivo diagnosis of cervical intraepithelial neoplasia using 337–nm exited laser–induced fluorescence", *Pro. Natl. Acad. Sci. USA*, 91:10193–10197.

Ramanujam et al. (1994), "Fluorescence Spectroscopy; A Diagnostic Tool for Cervical Intraepithelial Neoplasia (CIN)," *Gynecologic Oncology*, 52:31–38.

Reid et al. (1985), "Genital warts and cervical cancer, VII. An improved colposcopic index for differentiating benign papillomaviral infections from high–grade CIN," *Am. J. Obstet. Gynecol.*, 153(6):611–618.

Richards–Kortum et al. (1994), "Description and Performance of a Fiber–optic Confocal Fluorescence Spectrometer," *Applied Spectroscopy*, 48(3):350–355.

Romano et al. (1997), "Spectroscopic study of human leukocytes," *Physica Medica*, 13:291–295.

Ruprecht et al. (1995), "Image warping with scattered data interpolation methods," *IEEE Computer Graphics and Applications*, 37–43.

Sakuma (1985), "Quantitative Analysis of the Whiteness of the Atypical Cervical Transformation Zone", *The Journal of Reproductive Medicine*, 30(10):773–776.

Schmid (1999), "Lesion Detection in Dermatoscopic Images Using Anisotropic Diffusion and Morphological Flooding," *Proceedings of the International Conference on Image Processing (ICIP–99)*, 3:449–453.

Schmid (1999), "Segmentation and Symmetry Measure for Image Analysis: Application to Digital Dermatoscopy," *Ph.D. Thesis, Swiss Federal Institute of Technology (EPFL), Signal Processing Laboratory (LTS)*.

Schmitt et al. (1994), "Confocal Microscopy in Turbid Medica", *J. Opt. Soc. Am. A*, 11(8):2225–2235.

Schmitt et al. (1994), "Interferometric Versus Confocal Techniques for Imaging Microstructures in Turbid Biological Media", *Proc. SPIE*, 2135:1–12.

Schomacker et al. (1992), "Ultraviolet Laser–Induced Fluorescence of Colonic Polyps," *Gastroenterology*, 102:1155–1160.

Schomacker et al. (1992), "Ultraviolet Laser–Induced Fluorescence of Colonic Tissue; Basic Biology and Diagnostic Potential", *Lasers in Surgery and Medicine*, 12:63–78.

Schwartz (1993), "Real–time laser–scanning Confocal ratio imaging", *American Laboratory*, pp. 53–62.

Shafarenko et al. (1997), "Automatic Watershed Segmentation of Randomly Textured Color Images," *IEEE Transactions on Image Processing*, 6(11):1530–1544.

Shafi et al. (1995), "Modern image capture and data collection technology," *Clin. Obstet. Gynecol.*, 38(3):640–643.

Sheppard et al. (1978), "Depth of Field in the Scanning Microscope", *Optics Letters*, 3(3):115–117.

Szarewski et al., (1996), "Effect of smoking cessation on cervical lesions size," *Lancet*, 347:941–943.

Szeliski et al. (1997), "Spline–based image registration," *International Journal of Computer Vision*, 22(3):199–218.

Tadrous (2000), "Methods for Imaging the Structure and Function of Living Tissues and Cells: 2. Fluorescence Lifetime Imaging," *Journal of Pathology*, 191(3):229–234.

Thirion et al. (1999), "Deformation analysis to detect and quantify active lesions in three–dimensional medical image sequences," *IEEE Transactions on Medial Imaging*, 18(5):429–441.

Toglia et al. (1997), "Evaluation of colposcopic skills in an obstetrics and gynecology residency training program," *J. Lower Gen. Tract. Dis.*, 1(1):5–8.

Treameau et al. (1997), "A Region Growing and Merging Algorithm to Color Segmentation," *Pattern Recognition*, 30(7):1191–1203.

Van den Elsen et al. (1995), "Automatic registration of ct and mr brain images using correlation of geometrical features," *IEEE Transactions on medical imaging*, 14(2):384–396.

Vernon (1999), "Computation of Instantaneous Optical Flow Using the Phase of Fourier Components," *Image and Vision Computing*, 17:189–199.

Vincent et al. (1991), "Watersheds in Digital Spaces: An Efficient Algorithm Based on Immersion Simulations," *IEEE Transactions on Patterns Analysis and Machine Intelligence*, 13(6):583–598.

Vincent et al. (1993), "Morphological grayscale reconstruction in image analysis: Applications and efficient algorithms," *IEEE Transactions on Image Processing*, 2(2):176–201.

Wang et al. (1999), "Fast algorithms for the estimation of motion vectors," *IEEE Transactions on Image Processing*, 8(3):435–438.

Weng et al. (1997), "Three–Dimensional Surface Reconstruction Using Optical Flow for Medical Imaging," *IEEE Transactions on Medical Imaging*, 16(5):630–641.

Wilson, "The Role of the Pinhold in Confocal Imaging Systems", *Confocal Microscopy Handbook*, Chapter 11, 113–126.

Wolberg et al. (1998) "Image morphing: a survey," *The Visual Computer*, 14:360–372.

You et al. (1996), "Behavioral analysis of anisotropic diffusion in image processing," *IEEE Transactions on Image Processing*, 5(11):1539–1553.

Zahm et al. (1998), "Colposcopic appearance of cervical intraepithelial neoplasia is age dependent," *Am. J. Obstet. Gynecol.*, 179(5):1298–1304.

Zeger et al. (1992), "Globally optimal vector quantizer design by stochastic relaxation," *IEEE Transactions on Signal Processing*, 40(2):310–322.

Zeng et al. (1993), "A computerized autofluorescence and diffuse reflectance spectroanalyser system for in vivo skin studies," *Phys. Med. Biol.*, 38:231–240.

Zeng et al. (1997), "Optimization of fast block motion estimation algorithms," *IEEE Transactions on Circuits and Systems for Video Technology*, 7(6):833–844.

Zhang et al. (1999), "Shape from shading: a survey," *IEEE Transactions on Pattern Analysis and Machine Intelligence*, 21(8):690–706.

Zheng et al. (1991), "Estimation of illumination direction, albedo, and shape from shading," *IEEE Transactions on Pattern Analysis and Machine Intelligence*, 13(7):680–702.

Zhengfang et al. (1998), "Identification of Colonic Dysplasia and Neoplasia by Diffuse Reflectance Spectroscopy and Pattern Recognition Techniques," *Applied Spectroscopy*, 52(6):833–839.

European Search Report for Pending European Patent No. 02 01 9837, Jan. 14, 2004, 4 pgs.

Noble et al., "Automated, Nonrigid Alignment of Clinical Myocardial Contrast Echocardiography Image Sequences: Comparison with Manual Alignment," *Ultrasound in Medicine and Biology*, vol. 28, No. 1 (2002), pp. 115–123.

Ko et al., "Multiresolution Registration of Coronary Artery Image Sequences," *Internal Journal of Medical Informatics*, vol. 44 (1997), pp. 93–104.

* cited by examiner

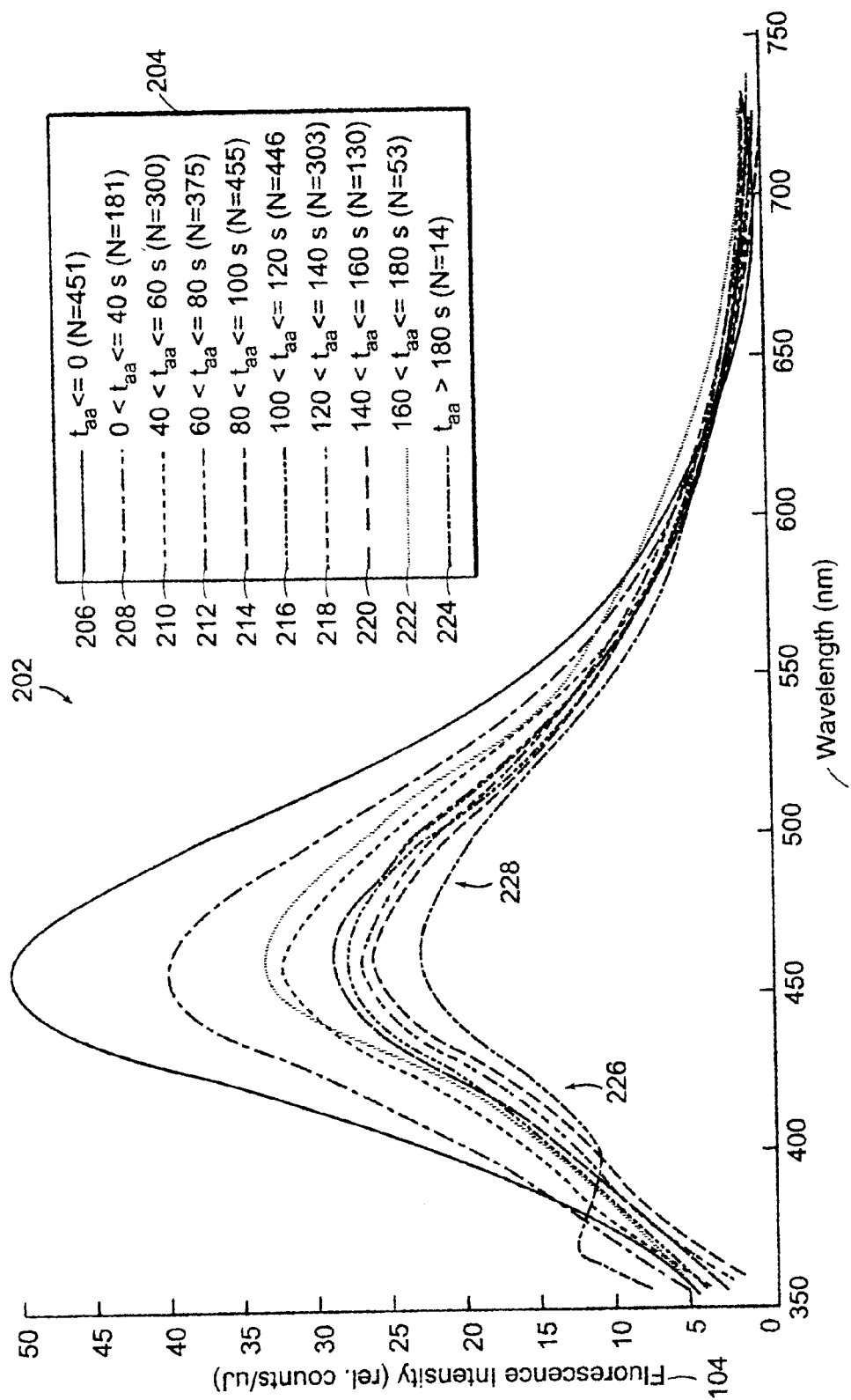

OPTIMAL WINDOWS FOR OBTAINING OPTICAL DATA FOR CHARACTERIZATION OF TISSUE SAMPLES

PRIOR APPLICATIONS

The present application claims the benefit of U.S. Provisional Patent Application Ser. No. 60/394,696, filed Jul. 9, 2002, which is hereby incorporated by reference.

FIELD OF THE INVENTION

The invention relates generally to spectroscopic methods. More particularly, the invention relates to the diagnosis of disease in tissue using spectral analysis and/or image analysis.

BACKGROUND OF THE INVENTION

Spectral analysis is used to diagnose disease in tissue. For example, data from spectral scans performed on the tissue of a patient are used to screen tissue for disease. Some diagnostic procedures include the application of a chemical contrast agent to the tissue in order to enhance the image and/or spectral response of the tissue for diagnosis. In an acetowhitening procedure, acetic acid is used as the contrast agent. Use of a contrast agent enhances the difference between data obtained from normal tissue and data obtained from abnormal or diseased tissue.

Current techniques do not suggest an optimal time period following application of a contrast agent within which to obtain spectral and/or image data for the diagnosis of disease, nor do current techniques suggest how such an optimal time period could be determined.

SUMMARY OF THE INVENTION

The invention provides optimal criteria for selecting spectral and/or image data from tissue that has been treated with a contrast agent for disease screening. In particular, it has been discovered that the sensitivity and specificity of optical diagnostic screening is improved by obtaining optical data at optimal time points after application of a contrast agent.

Accordingly, methods of the invention provide optimal windows in time for obtaining spectral data from tissue that has been treated with a contrast agent in order to improve the results of disease screening. The invention further provides methods for identifying such windows in the context of any optical diagnostic screen. Additionally, the invention provides methods for disease screening using kinetic data obtained across multiple diagnostic windows. Methods of the invention allow an optical diagnostic test to focus on data that will produce the highest diagnostic sensitivity and specificity with respect to the tissue being examined. Thus, the invention allows the identification of specific points in time after treatment of a tissue when spectral and/or image data most accurately reflects the health of the tissue being measured.

Time windows for observing selected spectral data may be determined empirically or from a database of known tissue responses to optical stimulation. For example, in one aspect the invention comprises building and using classification models to characterize the state of health of an unknown tissue sample from which optical signals are obtained. As used herein, an optical signal may comprise a discrete or continuous electromagnetic signal or any portion thereof, or the data representing such a signal. Essentially, optical diagnostic windows are based upon the points at which classification models perform best. In practice, optimal diagnostic windows of the invention may be predetermined segments of time following application of a contrast agent to a tissue. Optimal diagnostic windows may also be points in time at which an optical measurement meets a predetermined threshold or falls within a predetermined range, where the optical measurement represents the change of an optical signal received from the tissue following application of a contrast agent. For example, a window may be selected to include points in time at which the change in optical signal intensity from an initial condition is maximized. Finally, the optical measurement upon which a window is based may also reflect the rate of change in a spectral property obtained from the tissue.

In a preferred embodiment, optimal windows are determined by obtaining optical signals from reference tissue samples with known states of health at various times following application of a contrast agent. For example, one embodiment comprises obtaining a first set of optical signals from tissue samples having a known disease state, such as CIN 2/3 (grades 2 and/or 3 cervical intraepithelial neoplasia); obtaining a second set of optical signals from tissue samples having a different state of health, such as non-diseased; and categorizing each optical signal into "bins" according to the time it was obtained in relation to the time of application of contrast agent. The optical signal may comprise, for example, a reflectance spectrum, a fluorescence spectrum, a video image intensity signal, or any combination of these.

A measure of the difference between the optical signals associated with the two types of tissue is then obtained, for example, by determining a mean signal as a function of wavelength for each of the two types of tissue samples for each time bin, and using a discrimination function to determine a weighted measure of difference between the two mean optical signals obtained within a given time bin. This provides a measure of the difference between the mean optical signals of the two categories of tissue samples—diseased and healthy—weighted by the variance between optical signals of samples within each of the two categories.

In one embodiment, the invention further comprises developing a classification model for each time bin. After determining a measure of difference between the tissue types in each bin, an optimal window of time for differentiating between tissue types is determined by identifying at least one bin in which the measure of difference between the two tissue types is substantially maximized. For example, an optimal window of time may be chosen to include every time bin in which the respective classification model provides an accuracy of 70% or greater. Here, the optimal window describes a period of time following application of a contrast agent in which an optical signal can be obtained for purposes of classifying the state of health of the tissue sample with an accuracy of at least 70%.

An analogous embodiment comprises determining an optimal threshold or range of a measure of change of an optical signal to use in obtaining (or triggering the acquisition of) the same or a different signal for predicting the state of health of the sample. Instead of determining a specific, fixed window of time, this embodiment includes determining an optimal threshold of change in a signal, such as a video image whiteness intensity signal, after which an optical signal, such as a diffuse reflectance spectrum and/or a fluorescence spectrum, can be obtained to accurately characterize the state of health or other characteristic of the sample. An embodiment includes monitoring reflectance and/or fluorescence at a single or multiple wavelength(s), and upon reaching a threshold change from the initial condition, obtaining a full reflectance and/or fluorescence spectrum for use in diagnosing the region of tissue. This method allows for reduced data retrieval and monitoring since, in an embodiment, it involves continuous tracking of a single, partial-spectrum or discrete-wavelength "trigger" signal (instead of multiple, full-spectrum scans), followed by the acquisition of one or more spectral scans for use in diagnosis. Alternatively, the trigger may include more than one discrete-wavelength or partial-spectrum signal. The diagnostic data obtained will generally be more extensive than the trigger signal, and may include one or more complete sets of spectral data. The measure of change used to trigger obtaining one or more optical signals for tissue classification may be a weighted measure, and/or it may be a combination of measures of change of more than one signal. The signal(s) used for tissue classification/diagnosis may comprise one or more reflectance, fluorescence, and/or video signals. In one embodiment, two reflectance signals are obtained from the same region in order to provide a redundant signal for use when one reflectance signal is adversely affected by an artifact such as glare or shadow. Use of multiple types of classification signals may provide improved diagnostic accuracy over the use of a single type of signal. In one embodiment, a reflectance, fluorescence, and a video signal from a region of a tissue sample are all used in the classification of the region.

In a further embodiment, instead of determining an optimal threshold or range of a measure of change of an optical signal, an optimal threshold or range of a measure of the rate of change of an optical signal is determined. For example, the rate of change of reflectance and/or fluorescence is monitored at a single or multiple wavelength(s), and upon reaching a threshold rate of change, a full reflectance spectrum and/or fluorescence spectrum is acquired for use in diagnosing the region of tissue. The measure of rate of change used to trigger obtaining one or more optical signals for tissue classification may be a weighted measure, and/or it may be combination of measures of change of more than one signal. For example, the measured rate of change may be weighted by an initial signal intensity.

The invention also provides methods of disease screening using kinetic data from optical signals obtained at various times following application of a contrast agent. These methods comprise techniques for using specific features of fluorescence and diffuse reflectance spectra from reference cervical tissue samples of known states of health in order to diagnose a region of a tissue sample. These techniques allow monitoring of a particular optical signal from a test sample during a specified period of time following application of contrast agent to obtain pertinent kinetic data for characterizing the sample. For example, two or more time-separated measures of video intensity, fluorescence, and/or reflectance are obtained for a test sample at times between which it is known that an increase or decrease indicative of a given state of health occurs. It is therefore possible to determine whether this increase or decrease has occurred for the test sample, thereby indicating the sample may have a given state of health. Alternatively or additionally, a video, reflectance, and/or fluorescence signal from a test sample may be monitored over time to determine a time at which the signal reaches a maximum or minimum value. The time following application of contrast agent at which this minimum or maximum is reached can then be used to determine indication of a disease state in the test sample.

In one embodiment, data used as a baseline in determining an increase, decrease, maximum, or minimum as discussed above is not obtained before, but is obtained immediately following application of contrast agent to the tissue. In one case, the time period immediately following application of contrast agent is about ten seconds, and in another case, it is about five seconds, although other time periods are possible. This may be done to avoid error caused by movement of tissue or movement of the optical signal detection device upon application of contrast agent, particularly where such movement is not otherwise compensated for. Movement of tissue may cause error where a change from an initial condition is being monitored and the region of the tissue corresponding to the location at which the initial signal was obtained shifts following application of contrast agent.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 2A shows a graph depicting mean fluorescence spectra before application of acetic acid and at various times following the application of acetic acid for CIN 2/3 tissue (grades 2 and/or 3 cervical intraepithelial neoplasia).

DESCRIPTION OF THE ILLUSTRATIVE EMBODIMENTS

Figure 1A:
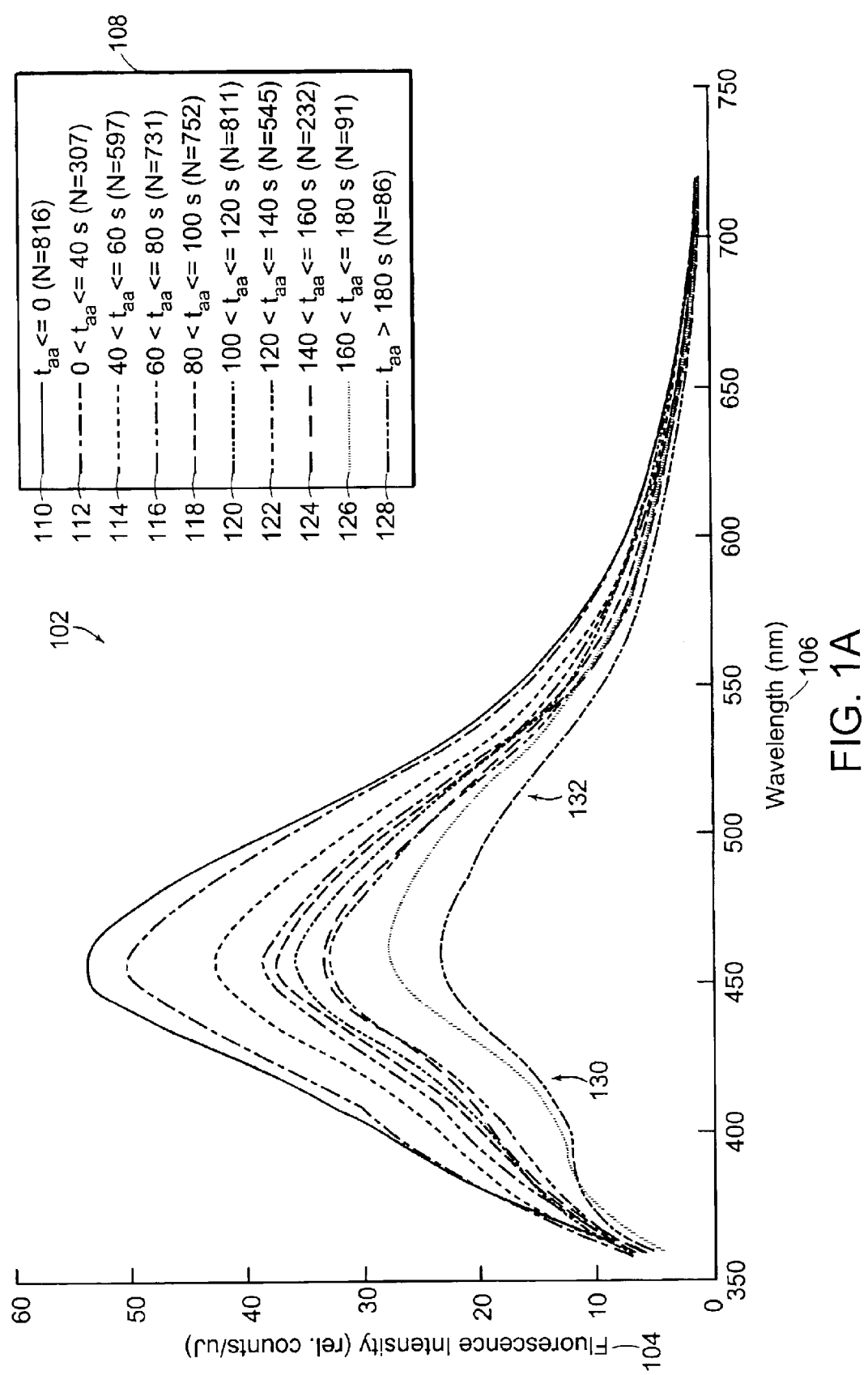
FIG. 1A shows a graph depicting mean fluorescence spectra before application of acetic acid and at various times following the application of acetic acid for NED tissue (no evidence of disease, confirmed by pathology).

The invention relates to methods for determining a characteristic of a tissue sample using spectral data and/or images obtained within an optimal window of time following the application of a chemical agent to the tissue sample. The invention provides methods of determining optimal windows of time. Similarly, the invention provides methods of determining criteria, based on a spectral amplitude or rate of amplitude change, for triggering the acquisition of an optical signal for classifying tissue. Finally, the invention comprises methods of diagnosing a tissue sample using spectral data and/or images obtained within an optimal window.

Application of the invention allows the diagnosis of regions of a tissue sample using various features of the time response of fluorescence and/or reflectance spectra following the application of a contrast agent such as acetic acid. For example, it is possible to diagnose a region of a tissue sample by determining a time at which a minimum value of fluorescence spectral intensity is reached following application of a contrast agent.

Methods of the invention are also used to analyze tissue samples, including cervical tissue, colorectal tissue, gastroesophageal tissue, urinary bladder tissue, lung tissue, or other tissue containing epithelial cells. The tissue may be analyzed in vivo or ex vivo, for example. Tissue samples are generally divided into regions, each having its own characteristic. This characteristic may be a state of health, such as intraepithelial neoplasia, mature and immature metaplasia, normal columnar epithelia, normal squamous epithelia, and cancer. Chemical contrast agents which are used in practice of the invention include acetic acid, formic acid, propionic acid, butyric acid, Lugol's iodine, Shiller's iodine, methylene blue, toluidine blue, indigo carmine, indocyanine green, fluorescein, and combinations comprising these agents. In embodiments where acetic acid is used, concentrations between about 3 volume percent and about 6 volume percent acetic acid are typical, although in some embodiments, concentrations outside this range may be used. In one embodiment, a 5 volume percent solution of acetic acid is used as contrast agent.

Optical signals used in practice of the invention comprise, for example, fluorescence, reflectance, Raman, infrared, and video signals. Video signals comprise images from standard black-and-white or color CCD cameras, as well as hyperspectral imaging signals based on fluorescence, reflectance, Raman, infrared, and other spectroscopic techniques. For example, an embodiment comprises analyzing an intensity component indicative of the "whiteness" of a pixel in an image during an acetowhitening test.

A preferred embodiment uses optical signals obtained from tissue samples within optimal windows of time. Obtaining an optical signal may comprise actually acquiring a signal within an optimal window of time, or, of course, simply triggering the acquisition of an optical signal within an optimal window of time. The optimal window of time may account for a delay between the triggering of the acquisition of a signal, and its actual acquisition. An embodiment of the invention may comprise determining an optimal window of time in which to trigger the acquisition of an optical signal, as well as determining an optimal window of time in which to actually acquire an optical signal.

One embodiment comprises determining an optimum time window in which to obtain spectra from cervical tissue such that sites indicative of grades 2 and 3 cervical intraepithelial neoplasia (CIN 2/3) can be separated from non-CIN 2/3 sites. Non-CIN 2/3 sites include sites with grade 1 cervical intraepithelial neoplasia (CIN 1), as well as NED sites (which include mature and immature metaplasia, and normal columnar and normal squamous epithelia). Alternately, sites indicative of high grade disease, CIN 2+, which includes CIN 2/3 categories, carcinoma in situ (CIS), and cancer, may be separated from non-high-grade-disease sites. In general, for any embodiment in which CIN 2/3 is used as a category for classification or characterization of tissue, the more expansive category CIN 2+ may be used alternatively. One embodiment comprises differentiating amongst three or more classification categories. Exemplary embodiments are described below and comprise analysis of the time response of diffuse reflectance and/or 337-nm fluorescence spectra of a set of reference tissue samples with regions having known states of health, as listed in the Appendix Table, to determine temporal characteristics indicative of the respective states of health. These characteristics are then used in building a model to determine a state of health of an unknown tissue sample. Other embodiments comprise analysis of fluorescence spectra using other excitation wavelengths, such as 380 nm and 460 nm, for example.

While the invention is particularly shown and described herein with reference to specific examples and specific embodiments, it should be understood by those skilled in the art that various changes in form and detail may be made therein without departing from the spirit and scope of the invention.

EXAMPLE 1

Analysis of the Temporal Evolution of Spectral Data from Reference Samples with Known States of Health.

Diffuse reflectance and/or 337-nm fluorescence emission spectra are taken from cervical tissue samples that are categorized as CIN 2/3 (having grades 2 and/or 3 cervical intraepithelial neoplasia), CIN 1 and NED (no evidence of disease, confirmed by pathology, including normal squamous tissue, normal columnar tissue, immature metaplasia tissue, and mature metaplasia tissue). All spectra are filtered then placed in the time bins indicated in Table 1. Data affected by arifacts such as glare, shadow, or obstructions may be removed and/of compensated for by using the technique disclosed in the co-owned U.S. patent application entitled, "Method and Apparatus for Identifying Spectral Artifacts," filed on Sep. 13, 2002, and identified by attorney docket number MDS-033, the contents of which are hereby incorporated by reference. Means spectra and standard deviations are calculated for the spectra in each time bin. Although not shown in this example, some embodiments use spectral and/or image data obtained at times greater than 180 s following application of contrast agent.

TABLE 1

Time bins for which means spectra are calculated in an exemplary embodiment

| Bin | Time after application of Acetic Acid (s) |
|---|---|
| 1 | t ≦ 0 |
| 2 | 0 < t ≦ 40 |
| 3 | 40 < t ≦ 60 |
| 4 | 60 < t ≦ 80 |
| 5 | 80 < t ≦ 100 |
| 6 | 100 < t ≦ 120 |
| 7 | 120 < t ≦ 140 |
| 8 | 140 < t ≦ 160 |
| 9 | 160 < t ≦ 180 |
| 10 | t > 180 |

FIGS. 1A, 1B, 2A, and 2B show mean fluorescence and reflectance spectra for exemplary healthy tissue (NED tissue—no evidence of disease, confirmed by pathology) and CIN 2/3 (grades 2 and/or 3 cervical intraepithelial neoplasia) tissue samples. These figures demonstrate the temporal effect of acetic acid on the spectral data. In the application of one embodiment, one or more characteristics of the time responses shown in FIGS. 1A, 1B, 2A, and 2B are determined. Subsequently, the time response of a sample of unknown type is obtained, and the sample is then diagnosed according to one or more features of the response, compared against those of the known sample set.

FIG. 1A shows a graph 102 depicting mean fluorescence spectra for each of the 10 time bins 108 of Table 1 for NED tissue (no evidence of disease, confirmed by pathology). Mean fluorescence intensity (relative counts/µJ) 104 is plotted as a function of wavelength (nm) 106 for each time bin shown in the legend 108. The curve corresponding to the first time bin 110 is a graph of the mean fluorescence intensity as a function of wavelength for data collected prior to acetic acid application, and the curve corresponding to the last time bin 128 is a graph of the mean fluorescence intensity as a function of wavelength for data collected at times greater than 180 seconds (with an average of about 210 seconds). Each of the curves in between (112, 114, 116, 118, 120, 122, 124, 126) is a graph of the mean fluorescence intensity as a function of wavelength for data collected in the respective time bin shown in the legend 108. The value of N shown in the legend 108 beside each curve denotes the number of spectra that are in the respective time bin for this particular embodiment.

Figure 1B:
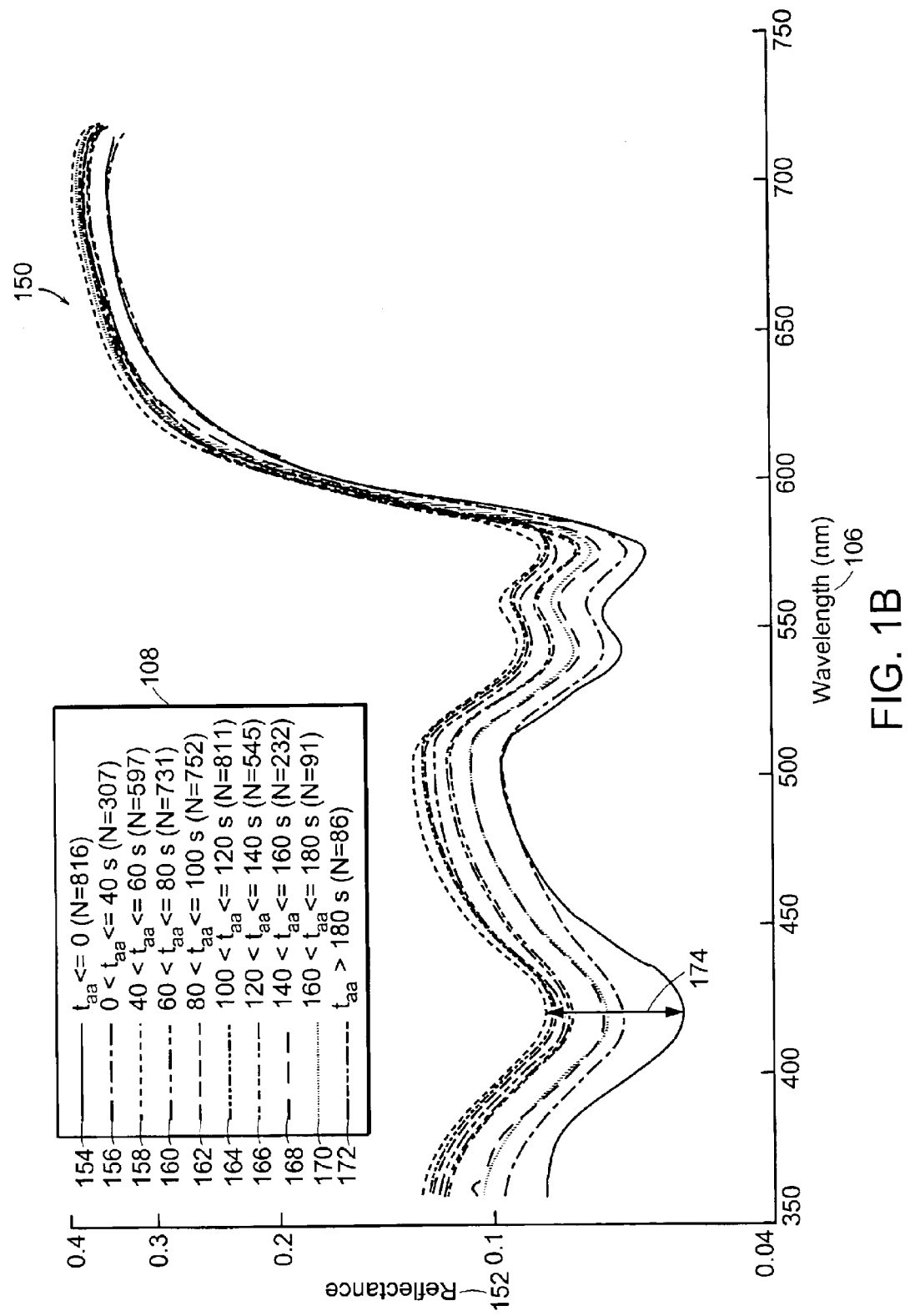
FIG. 1B shows a graph depicting mean reflectance spectra before application of acetic acid and at various times following the application of acetic acid for NED tissue (no evidence of disease, confirmed by pathology).

FIG. 1B shows a graph 150 depicting mean reflectance spectra for each of the 10 time bins 108 of Table 1 for NED tissue (no evidence of disease, confirmed by pathology). Mean reflectance 152 is plotted as a function of wavelength (nm) 106 for each time bin shown in the legend 108. The curve corresponding to the first time bin 154 is a graph of the mean reflectance as a function of wavelength for data collected prior to acetic acid application, and the curve corresponding to the last time bin 172 is a graph of the mean reflectance as a function of wavelength for data collected at times greater than 180 seconds (with an average of about 210 seconds). Each of the curves in between (156, 158, 160, 162, 164, 166, 168, 170) is a graph of the mean reflectance as a function of wavelength for data collected in the respective time bin shown in the legend 108. The value of N shown in the legend 108 beside each curve denotes the number of spectra that are in the respective time bin for this particular embodiment.

FIG. 2A shows a graph 202 depicting mean fluorescence spectra for each of the 10 time bins 204 of Table 1 for CIN 2/3 tissue (grades 2 and/or 3 cervical intraepithelial neoplasia). Mean fluorescence intensity (relative counts/µJ) 104 is plotted as a function of wavelength (nm) 106 for each time bin shown in the legend 204. The curve corresponding to the first time bin 206 is a graph of the mean fluorescence intensity as a function of wavelength for data collected prior to acetic acid application, and the curve corresponding to the last time bin 224 is a graph of the mean fluorescence intensity as a function of wavelength for data collected at times greater than 180 seconds (with an average of about 210 seconds). Each of the curves in between (208, 210, 212, 214, 216, 218, 220, 220) is a graph of the mean fluorescence intensity as a function of wavelength for data collected in the respective time bin shown in the legend 204. The value of N shown in the legend 204 beside each curve denotes the number of spectra that are in the respective time bin for this particular embodiment.

Figure 2B:
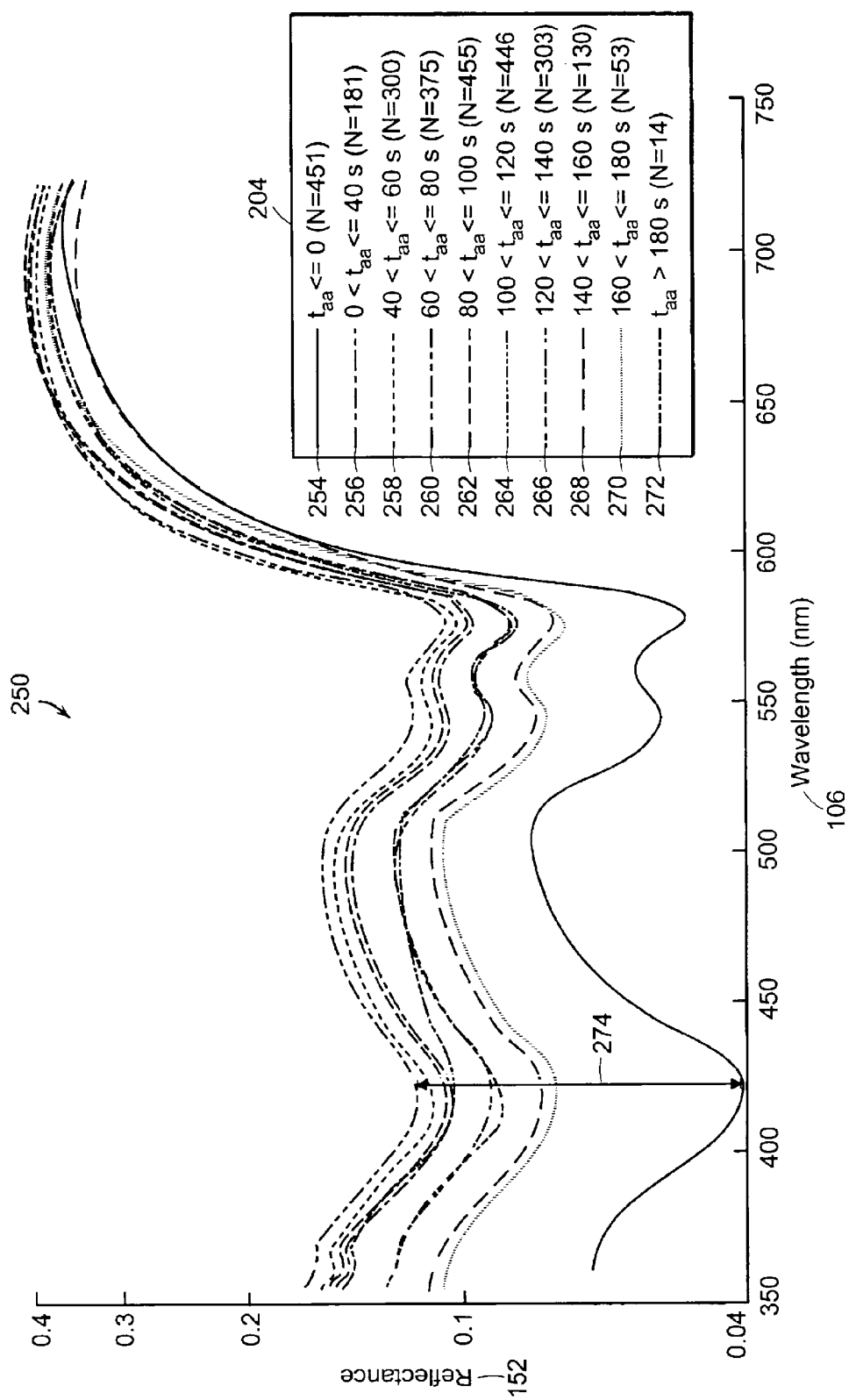
FIG. 2B shows a graph depicting mean reflectance spectra before application of acetic acid and at various times following the application of acetic acid for CIN 2/3 tissue (grades 2 and/or 3 cervical intraepithelial neoplasia).

FIG. 2B shows a graph 250 depicting mean reflectance spectra for each of the 10 time bins 204 of Table 1 for CIN 2/3 tissue (grades 2 and/or 3 cervical intraepithelial neoplasia). Mean reflectance 152 is plotted as a function of wavelength (nm) 106 for each time bin shown in the legend 204. The curve corresponding to the first time bin 254 is a graph of the mean reflectance as a function of wavelength for data collected prior to acetic acid application, and the curve corresponding to the last time bin 272 is a graph of the mean reflectance as a function of wavelength for data collected at times greater than 180 seconds (with an average of about 210 seconds). Each of the curves in between (256, 258, 260, 262, 264, 266, 268, 270) is a graph of the mean reflectance as a function of wavelength for data collected in the respective time bin shown in the legend 204. The value of N shown in the legend 204 beside each curve denotes the number of spectra that are in the respective time bin for this particular embodiment.

EXAMPLE 2

Analysis of Optical Kinetic Data from Reference Samples with Known States of Health.

Figure 3A:
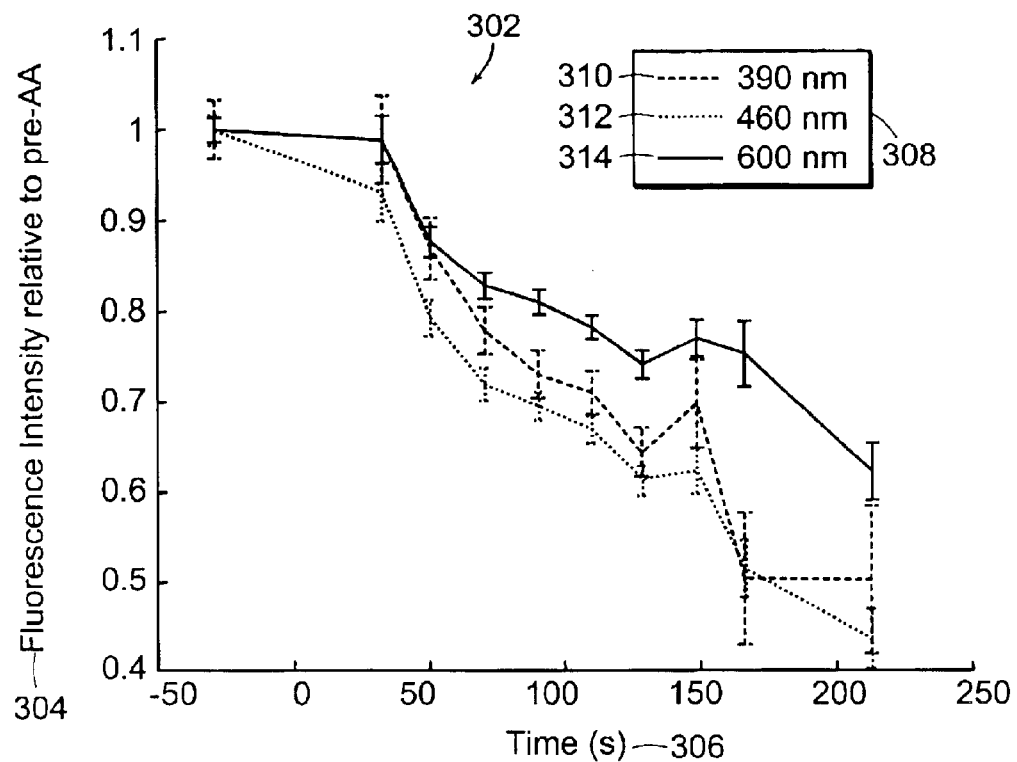
FIG. 3A shows a graph depicting fluorescence intensity at three different wavelengths relative to pre-AA (fluorescence before application of acetic acid) as a function of time following application of acetic acid for NED tissue.
Figure 3B:
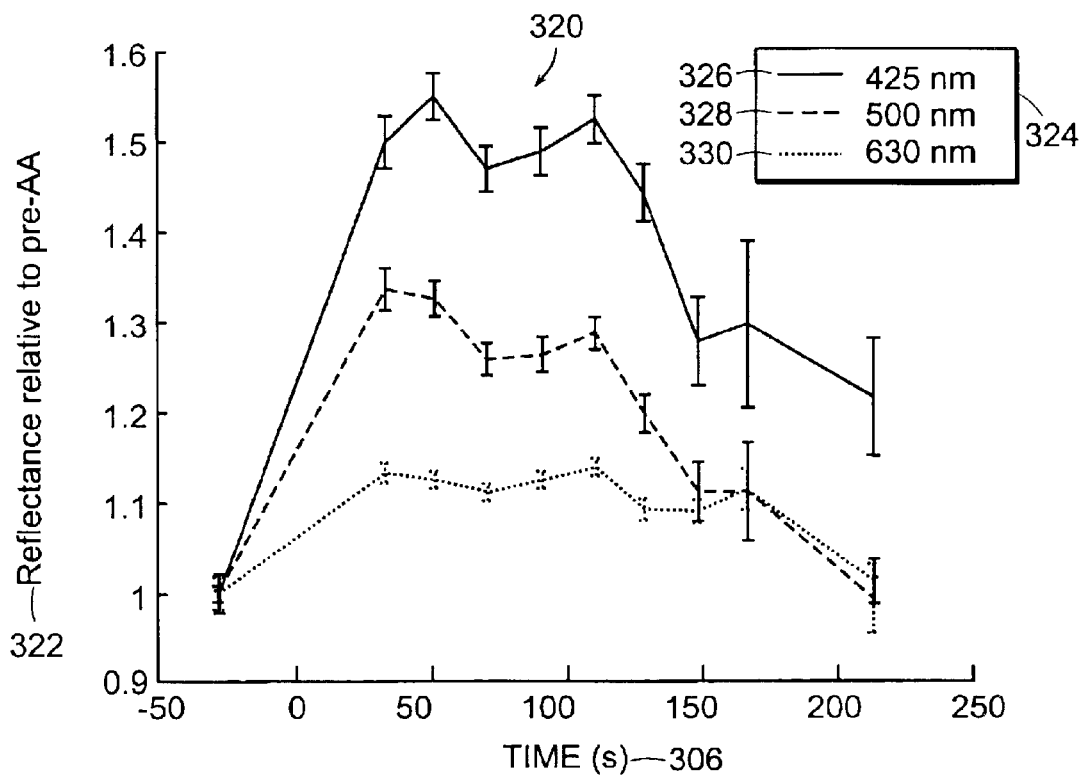
FIG. 3B shows a graph depicting reflectance at three different wavelengths relative to pre-AA (reflectance before application of acetic acid) as a function of time following application of acetic acid for NED tissue.
Figure 3C:
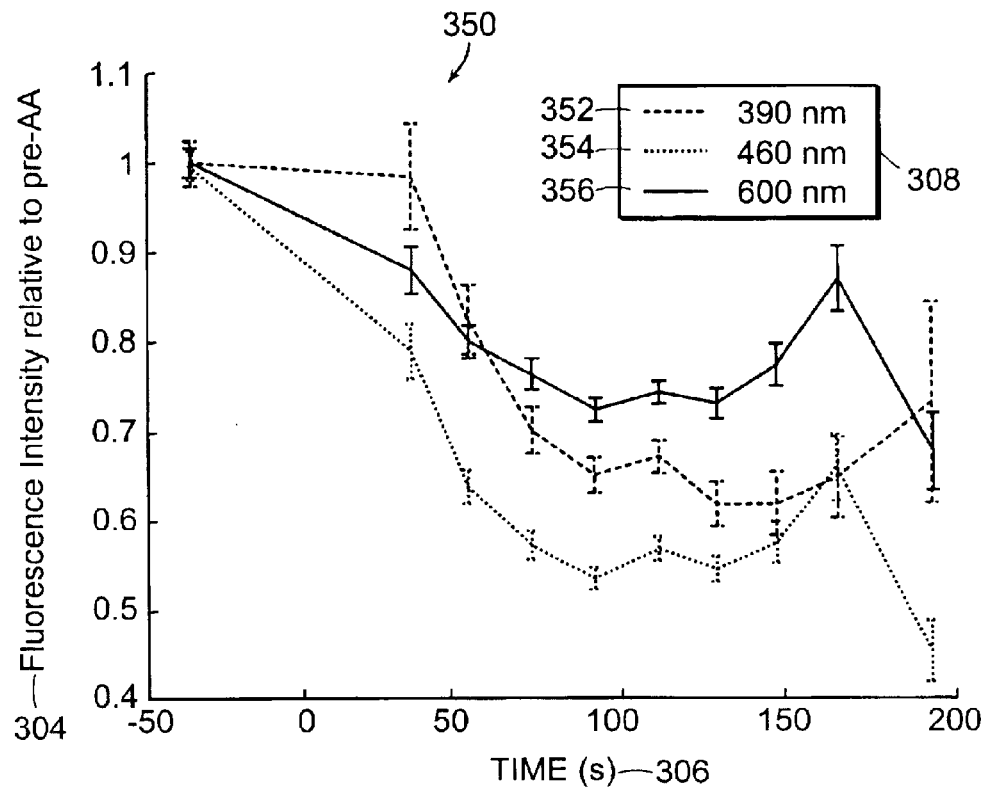
FIG. 3C shows a graph depicting fluorescence intensity at three different wavelengths relative to pre-AA (fluorescence before application of acetic acid) as a function of time following application of acetic acid for CIN 2/3 tissue.
Figure 3D:
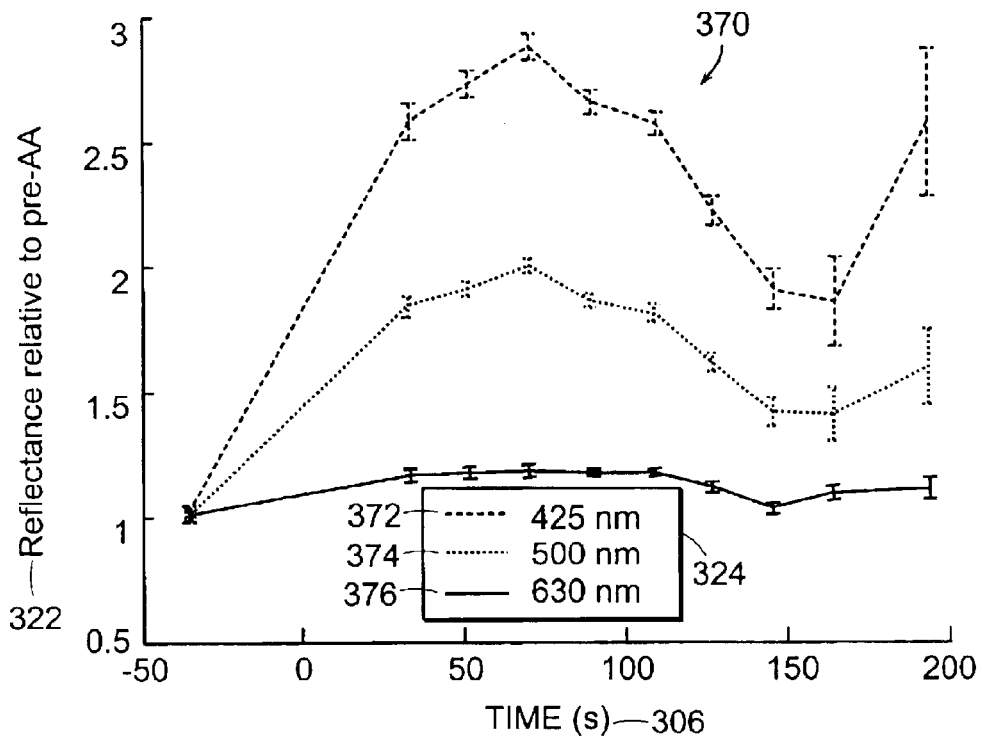
FIG. 3D shows a graph depicting reflectance at three different wavelengths relative to pre-AA (reflectance before application of acetic acid) as a function of time following application of acetic acid for CIN 2/3 tissue.

Data from FIGS. 1A, 1B, 2A, and 2B are further analyzed as shown in FIGS. 3A, 3B, 3C, and 3D. FIG. 3A shows a graph 302 depicting the time response of fluorescence intensity relative to pre-AA (fluorescence prior to application of acetic acid) 304 of NED tissue at 390, 460 and 600 nm wavelengths following application of acetic acid. FIG. 3B shows a graph 320 depicting the time response of reflectance relative to pre-AA 322 for NED tissue at 425, 500, and 630 nm wavelengths following application of acetic acid. FIG. 3C shows a graph 350 depicting the time response of fluorescence intensity relative to pre-AA 304 of CIN 2/3 tissue at 390, 460, and 600 nm wavelengths following application of acetic acid. FIG. 3D shows a graph 370 depicting the time response of reflectance relative to pre-AA 322 for CIN 2/3 tissue at 425, 500, and 630 nm wavelengths following application of acetic acid.

The fluorescence intensity in the NED group continues to drop over the time period studied while some recovery is seen in the fluorescence intensity of the CIN 2/3 group. FIG. 3A reveals a continuous drop in fluorescence for the NED group over the measurement period at the three wavelengths. In contrast, FIG. 3C shows partial recovery at all three wavelengths for CIN 2/3 tissue. Each of the curves representing CIN 2/3 tissue labeled 352, 354, and 356 in FIG. 3C demonstrates a generalized local minimum at a time from about 70 to about 130 seconds following application of acetic acid, whereas each of the curves representing NED tissue labeled 310, 312, and 314 in FIG. 3A does not show such a local minimum.

The fluorescence and reflectance kinetics are similar for the CIN 2/3 group but differ for the NED group. Partial recovery (return toward initial condition) is noted in both the reflectance and the fluorescence curves at all 3 wavelengths for CIN 2/3 tissue, as shown in the curves labeled 352, 354, 356, 372, 374, and 376 in FIG. 3C and FIG. 3D. However, partial recovery is noted only in the reflectance curves for NED tissue (curves 326, 328, and 330 of FIG. 3B), while the NED fluorescence intensities continue to drop (curves 310, 312, and 314 of FIG. 3A).

The magnitude of change in the time response of reflectance and fluorescence data following application of acetic acid is different between the CIN 2/3 group and the NED group. The relative maximum change in reflectivity at about 425 nm is about twice as large for CIN 2/3 (i.e. line segment 274 in FIG. 2B) compared to non-CIN (i.e. line segment 174 in FIG. 1B), while the maximum change for fluorescence is approximately equivalent for CIN 2/3 and non-CIN samples. Here, the magnitude of change in the reflectance signal depends on tissue type while the magnitude of change in the fluorescence signal does not depend on tissue type.

The time to reach the maximum change in fluorescence is delayed for NED spectra. This is shown by comparing curves 310, 312, and 314 of FIG. 3A with curves 352, 354, and 356 of FIG. 3C. It is therefore possible, for example, to use the time required to reach a minimum value of fluorescence spectral intensity to distinguish CIN 2/3 from NED samples.

The fluorescence line-shape changes with time post acetic acid, particularly at later times where a valley at about 420 nm and a band at about 510 nm become more distinct. The valley at about 420 nm is shown in FIG. 1A at reference number 130 and in FIG. 2A at reference number 226, while the band at about 510 nm can be seen in FIG. 1A at reference number 132 and in FIG. 2A at reference number 228. One explanation for this change is that collagen and NADH decrease tissue fluorescence and FAD increases tissue fluorescence. Upon introduction of a change in pH from 7 to 3.5, the fluorescence intensity of NADH decreases by a factor of two while FAD increases six-fold. Increased scattering in the epithelial layer would decrease the contribution of collagen fluorescence from the submucosal layer. Characterization of such changes in spectral curve shape is useful, for example, in distinguishing tissue types.

In one embodiment, an optimal window for obtaining spectral and/or image data is a period of time in which there is a peak "whitening" as seen in image and/or reflectance data. In another embodiment, an optimal window is a period of time in which there is a peak "darkening" of fluorescence of the tissue. Still another embodiment uses a subset of the union of the two optimal windows above. FIGS. 1A, 1B, 2A, 2B, 3A, 3B, 3C, and 3D demonstrate "whitening" of reflectance and "darkening" of fluorescence as a function of wavelength and time following application of acetic acid. The maximum change observed in the CIN 2/3 group is determined from the data shown in FIGS. 2A, 2B, 3C, and 3D. Here, the peak "darkening" of the fluorescence data lags peak "whitening" of the reflectance data. From the reflectance data, the window for peak whitening lies between about 30 s and about 110 s following the application of acetic acid with a maximum at about 70 s. In one embodiment, the peak whitening window lies between about 30 s and about 130 s; and in another embodiment from about 20 s to about 180 s. For fluorescence, the peak "darkening" window lies between about 50 s and about 150 s with a minimum at about 80 s. In one embodiment, the peak darkening window lies between about 60 s and about 220 s. Peak "whitening" for the non-CIN reflectance spectra is less intense but similar in shape to that found for CIN 2/3. Peak darkening in non-CIN fluorescence appears later than in CIN 2/3 fluorescence.

Figure 4A:
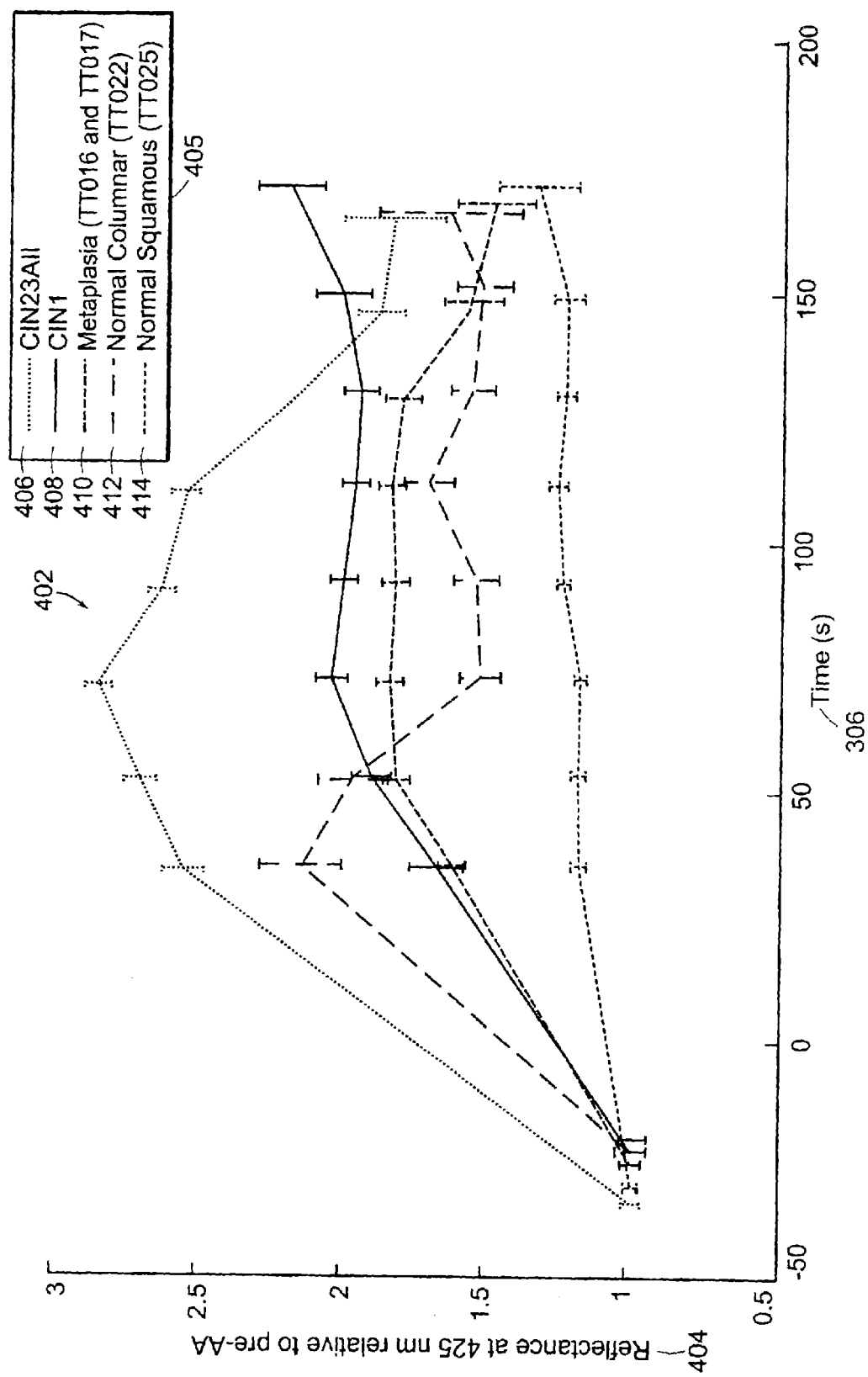
FIG. 4A shows a graph depicting reflectance relative to pre-AA at 425 nm as a function of time following application of acetic acid for various tissue types.
Figure 4B:
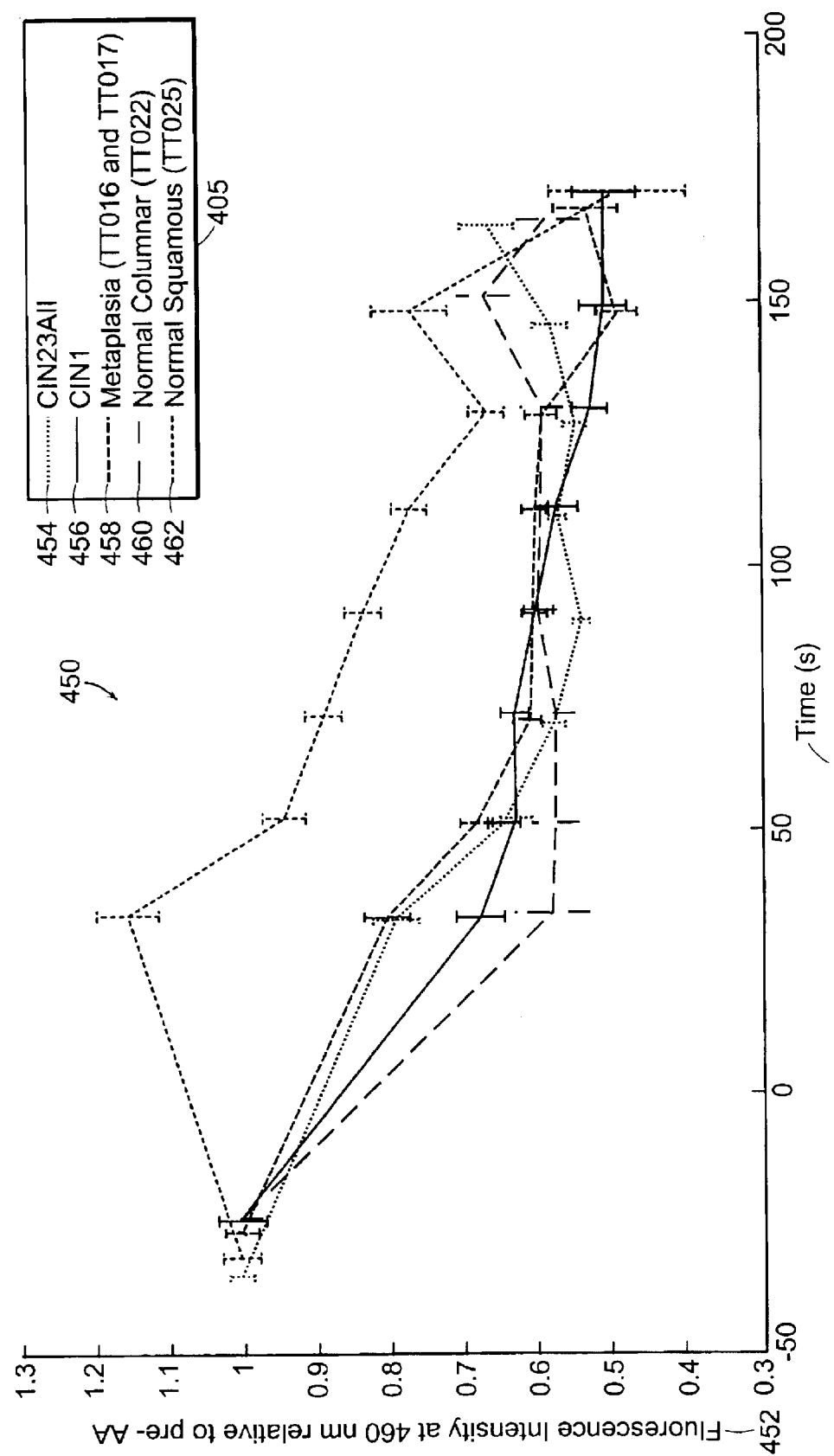
FIG. 4B shows a graph depicting fluorescence relative to pre-AA at 460 nm as a function of time following application of acetic acid for various tissue types.

FIGS. 4A and 4B depict the influence of acetic acid on reflectance and fluorescence intensities at about 425 nm and about 460 nm, respectively, for various reference tissue classes. These classes include CIN 2/3 (curves 406 and 454), CIN 1 (curves 408 and 456), metaplasia TT016 and TT017 (curves 410 and 458), normal columnar TT022 (curves 412 and 460) and normal squamous TT025 (curves 414 and 462) tissues, as shown in FIGS. 4A and 4B. In general, the reflectance curves of FIG. 4A show some distinct differences with tissue type, with CIN 2/3 tissue (curve 406) having the largest change. Columnar epithelial tissue (curve 412) shows rapid relatively intense whitening followed by rapid recovery while squamous epithelial tissue (curve 414) has a weak, slow response with very little recovery. Metaplastic tissues (curve 410) and tissue with CIN 1 (curve 408) have similar behavior with a relatively fast increase and decay. The acetowhitening response of all tissue groups ride on top of a slowing, increasing background, thereby suggesting a secondary response to acetic acid. This secondary response is most distinct in the CIN 1 group and appears to be the predominant response in the normal squamous group.

The magnitude of the acetodarkening effect for fluorescence is similar independent of tissue type, as shown in FIG. 4B. The time to reach a minimum fluorescence is different for different tissue classes, with normal squamous tissue (curve 462) having the slowest response and normal columnar tissue (curve 460) having the fastest response. The response for CIN 2/3 (curve 454), CIN 1 (curve 456), and metaplastic tissues (curve 458) are very similar. There is partial recovery from the acetic acid effect in the CIN 2/3 group (curve 454).

EXAMPLE 3

Using a Discrimination Function to Determine Optimal Windows for Obtaining Diagnostic Optical Data.

An embodiment of the invention comprises determining an optimum window for obtaining diagnostic spectral data using fluorescence and/or reflectance time-response data as shown in the above figures, and as discussed above. In one embodiment, an optimum window is determined by tracking the difference between spectral data of various tissue types using a discrimination function.

In one embodiment, the discrimination function shown below in Equation (1) is used to extract differences between tissue types:

$$D(\lambda) = \frac{\mu(\text{test}(\lambda))_{NED\ PATH1} - \mu(\text{test}(\lambda))_{CIN23ALL}}{\sqrt{\sigma^2(\text{test}(\lambda))_{NED\ PATH1} = \sigma^2(\text{test}(\lambda))_{CIN23ALL}}} \quad (1)$$

The quantity $\mu$ corresponds to the mean optical signal and $\sigma$ corresponds to the standard deviation. In one embodiment, the optical signal includes diffuse reflectance. In another embodiment, the optical signal includes 337-nm fluorescence emission spectra. Other embodiments use fluorescence emission spectra at another excitation wavelength such as 380 nm and 460 nm. In still other embodiments, the optical signal is a video signal, Raman signal, or infrared signal. Some embodiments comprise using difference spectra calculated between different phases of acetowhitening, using various normalization schema, and/or using various combinations of spectral data and/or image data as discussed above.

One embodiment comprises developing linear discriminant analysis models using spectra from each time bin as shown in Table 1. Alternatively, nonlinear discriminant analysis models may be developed. Generally, models are trained using reflectance and fluorescence data separately, although some embodiments comprise use of both data types to train a model. In exemplary embodiments discussed below, reflectance and fluorescence intensities are down-sampled to one value every 10 nm between 360 and 720 nm. A model is trained by adding and removing intensities in a forward manner, continuously repeating the process until the model converges such that additional intensities do not appreciably improve tissue classification. Testing is performed by a leave-one-spectrum-out jack-knife process.

Figure 5:
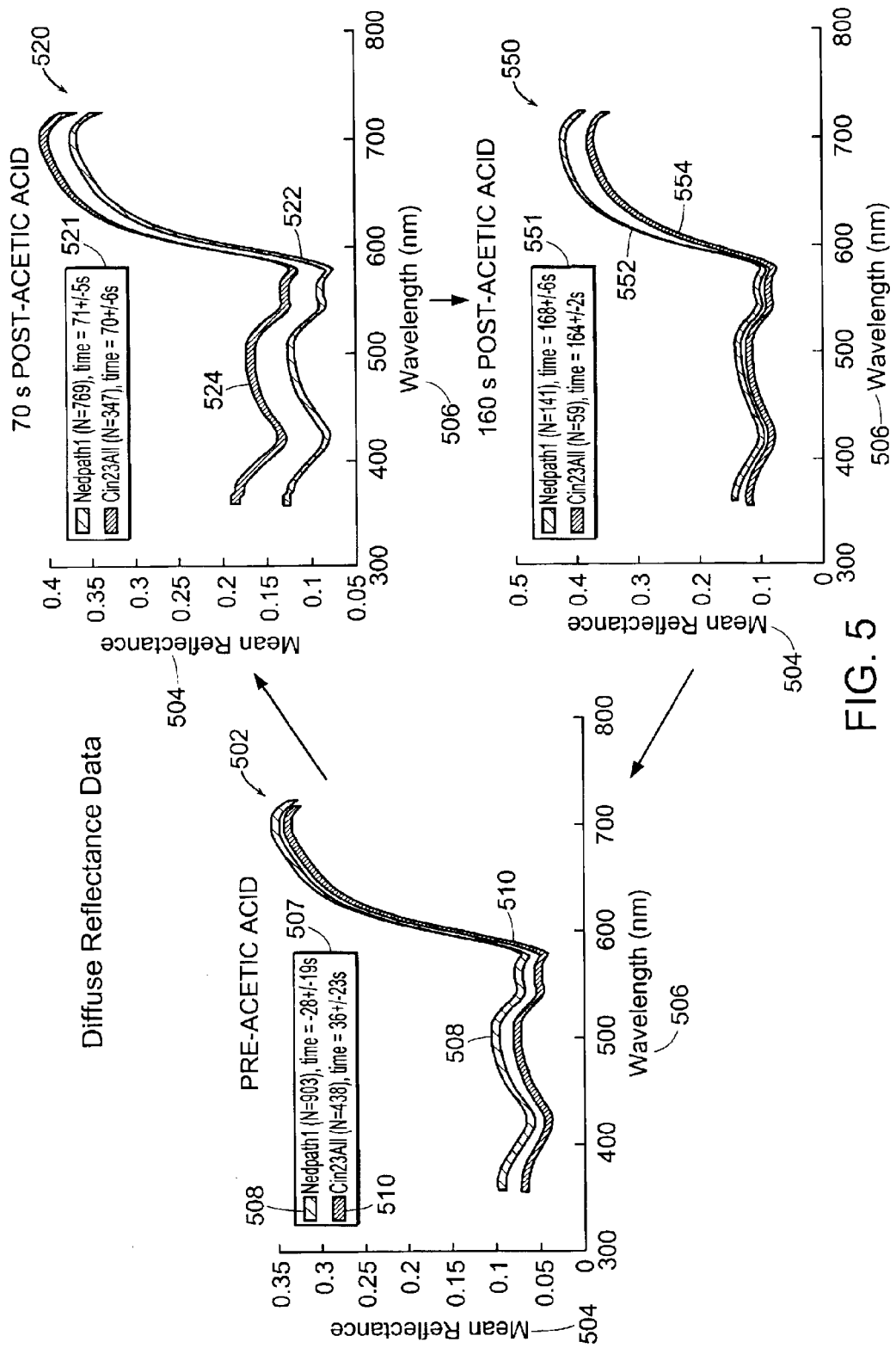
FIG. 5 shows a series of graphs depicting mean reflectance spectra for CIN 2/3 and non-CIN 2/3 (NED and CIN 1) tissues at a time prior to application of acetic acid, at a time corresponding to maximum whitening, and at a time corresponding to the latest time at which data was obtained.

FIG. 5 shows the difference between the mean reflectance spectra for non-CIN 2/3 tissues (including CIN 1 and NED tissues) and CIN 2/3 tissues at three times—at a time prior to the application of acetic acid (graph 502), at a time corresponding to maximum whitening (graph 520, about 60–80 seconds post-AA), and at a time corresponding to the latest time period in which data was obtained (graph 550, about 160–180 seconds post-AA). Here, the time corresponding to maximum whitening was determined from reflectance data, and occurs between about 60 seconds and 80 seconds following application of acetic acid. In the absence of acetic acid, the reflectance spectra for CIN 2/3 (curve 510 of graph 502 in FIG. 5) are on average lower than non-CIN 2/3 tissue (curve 508 of graph 502 in FIG. 5). Following the application of acetic acid, a reversal is noted with CIN 2/3 tissues having higher reflectance than the other tissues. The reflectance of CIN 2/3 and non-CIN 2/3 tissues increase with acetic acid, with CIN 2/3 showing a larger relative percent change (compare curves 522 and 524 of graph 520 in FIG. 5). From about 160 s to about 180 s following acetic acid, the reflectance of CIN 2/3 tissue begins to return to the pre-acetic acid state, while the reflectance of the non-CIN 2/3 group continues to increase (compare curves 552 and 554 of graph 550 in FIG. 5)

Figure 6:
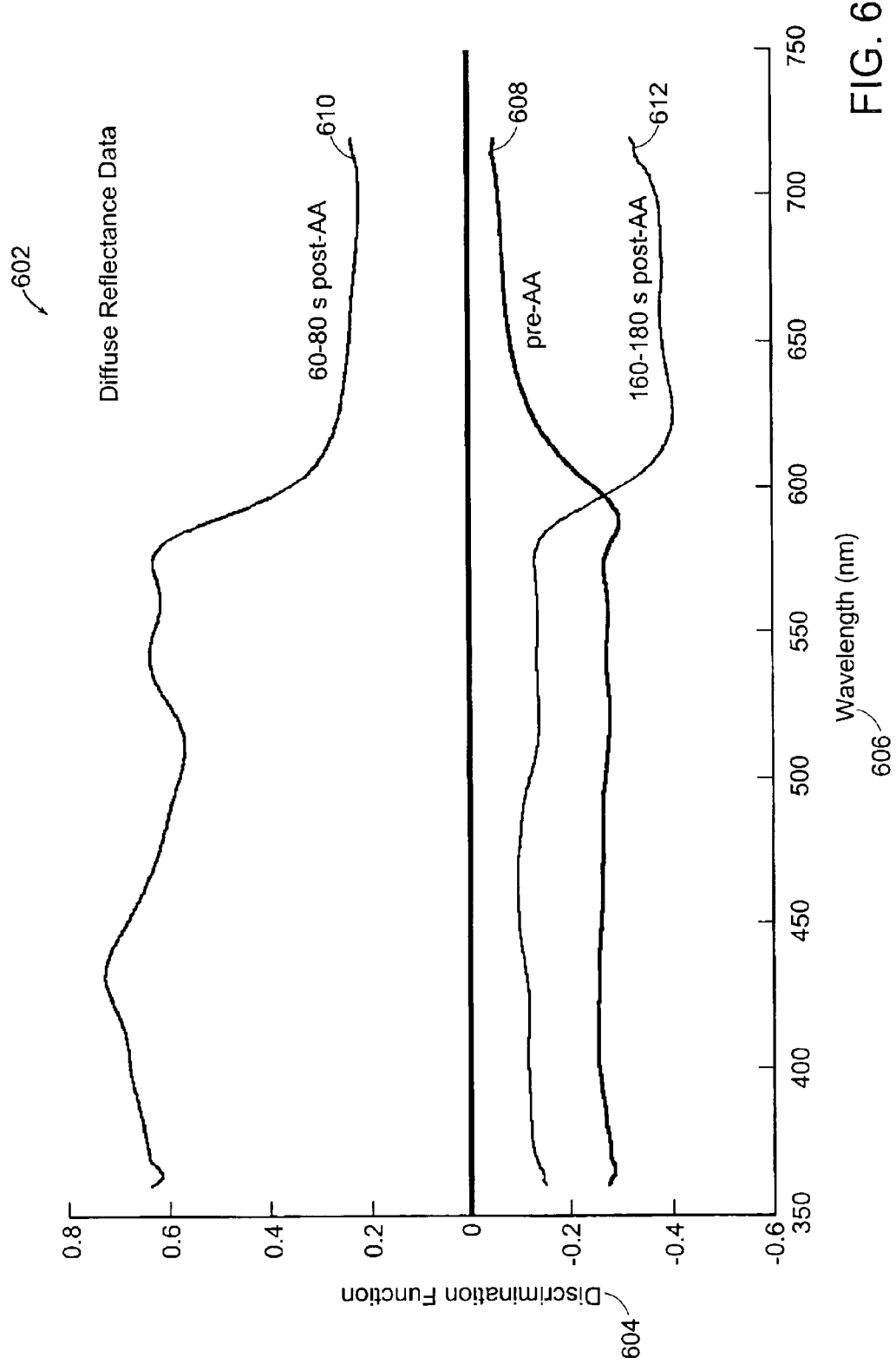
FIG. 6 shows a graph depicting the reflectance discrimination function spectra useful for differentiating between CIN 2/3 and non-CIN 2/3 (NED and CIN 1) tissues.

In one embodiment, discrimination function 'spectra' are calculated from the reflectance spectra of CIN 2/3 and non-CIN 2/3 tissues shown in FIG. 5. In one example, discrimination function spectra comprise values of the discrimination function in Equation (1) determined as a function of wavelength for sets of spectral data obtained at various times. FIG. 6 shows a graph 602 depicting the discrimination function spectra evaluated using the diffuse reflectance data of FIG. 5 obtained prior to application of acetic acid, and at two times post-AA. Curve 608 corresponds to the discrimination function 604 evaluated as a function of wavelength 606 using non-CIN 2/3 data and CIN 2/3 data obtained prior to application of acetic acid. Curve 610 corresponds to the discrimination function 604 evaluated as a function of wavelength 606 using non-CIN 2/3 data and CIN 2/3 data obtained between about 60 and about 80 seconds after application of acetic acid; and curve 612 corresponds to the discrimination function 604 evaluated as a function of wavelength 606 using non-CIN 2/3 data and CIN 2/3 data obtained between about 160 and about 180 seconds after application of acetic acid. Distinguishing between CIN 2/3 and non-CIN 2/3 tissues using reflectance data is improved with the application of acetic acid. Here, the largest differences (for example, the largest absolute values of discrimination function) are found from data measured from about 60 s to about 80 s post-acetic acid (curve 610), and these agree with the differences seen in the mean reflectance spectra of FIG. 5 (curves 522 and 524 of graph 520 in FIG. 5).

Performing multivariate linear regression analysis addresses wavelength interdependence in the development of a classification model. An application of one embodiment comprises classifying data represented in the CIN 2/3, CIN 1, and NED categories in the Appendix Table into CIN 2/3 and non-CIN 2/3 categories by using classification models developed from the reflectance data shown in FIG. 5. Here, reflectance intensities are down-sampled to one about every 10 nm between about 360 nm and about 720 nm. The model is trained by adding intensities in a forward-stepped manner. Testing is performed with a leave-one-spectrum-out jack-knife process. The result of this analysis shows which wavelengths best separate CIN 2/3 from non-CIN 2/3, as shown in table 2 for an exemplary embodiment.

TABLE 2

Forwarded selected best reflectance wavelengths for classifying CIN 2/3 from non-CIN 2/3 spectra obtained at different times pre and post-AA.

| Time from AA (s) | LDA Model Input Wavelengths (nm) | Accuracy |
|---|---|---|
| −30 | 370 400 420 440 530 570 590 610 | 66 |
| 30 | 420 430 450 600 | 74 |
| 50 | 360 400 420 430 580 600 | 74 |
| 70 | 360 400 420 430 540 600 | 75 |
| 90 | 360 420 430 540 590 | 73 |
| 110 | 360 440 530 540 590 | 71 |
| 130 | 360 420 430 540 590 | 71 |
| 150 | 370 400 430 440 540 620 660 690 720 | 72 |
| 170 | 490 530 570 630 650 | 75 |

The two best models for separating CIN 2/3 and non-CIN 2/3 for this embodiment include the model using reflectance data obtained at peak CIN 2/3 whitening (from about 60 s to about 80 s) and the model using reflectance data from the latest time measured (from about 160 s to about 180 s post acetic acid). The first model uses input wavelengths between about 360 and about 600 nm, while the second model uses more red-shifted wavelengths between about 490 and about 650 nm. This is consistent with the behavior of the discrimination function spectra shown in FIG. 6.

Figure 7:
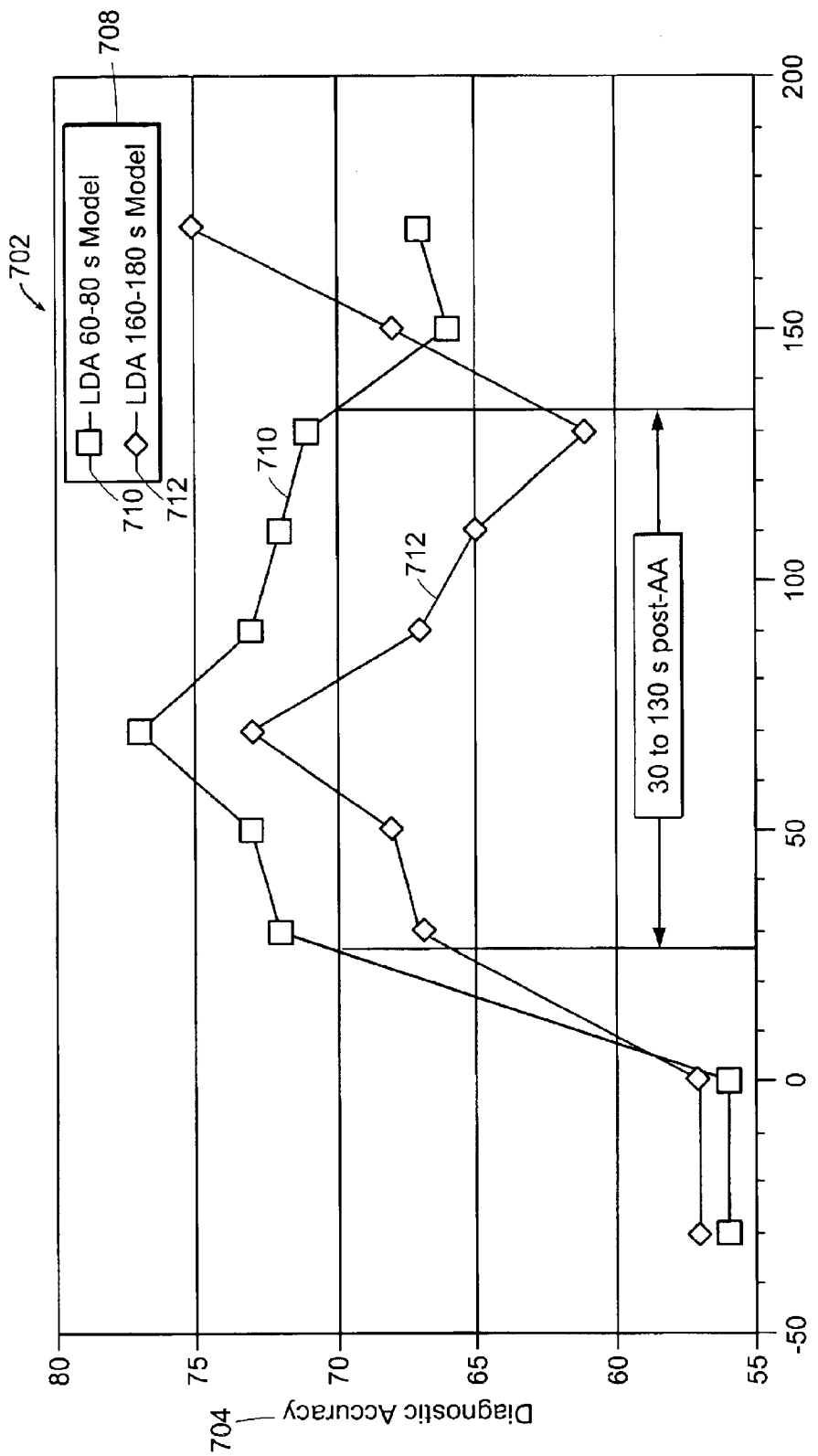
FIG. 7 shows a graph depicting the performance of two LDA (linear discriminant analysis) models as applied to reflectance data obtained at various times following application of acetic acid; one of the models is based on data obtained between 60 and 80 seconds following application of acetic acid, and the other model is based on data obtained between 160 and 180 seconds following application of acetic acid.

FIG. 7 demonstrates one method of determining an optimal window for obtaining reflectance spectral data in the diagnosis of the state of health of a region of a sample as CIN 2/3 or non-CIN 2/3. FIG. 7 shows a graph 702 depicting the performance of the two LDA models described in Table 2 above as applied to reflectance spectral data obtained at various times following application of acetic acid 706. Curve 710 in FIG. 7 is a plot of the diagnostic accuracy of the LDA model based on reflectance spectral data obtained between about 60 and about 80 seconds ("peak whitening model") as applied to reflectance spectra from the bins of Table 1, and curve 712 in FIG. 7 is a plot of the diagnostic accuracy of the LDA model based on reflectance spectral data obtained between about 160 and about 180 seconds, as applied to reflectance spectra from the bins of Table 1. For the peak-whitening model, the highest accuracy was obtained at about 70 s, while accuracies greater than 70% were obtained with spectra collected in a window between about 30 s and about 130 s. The 160–180 s model had a narrower window around 70 s, but performs better at longer times.

Figure 8:
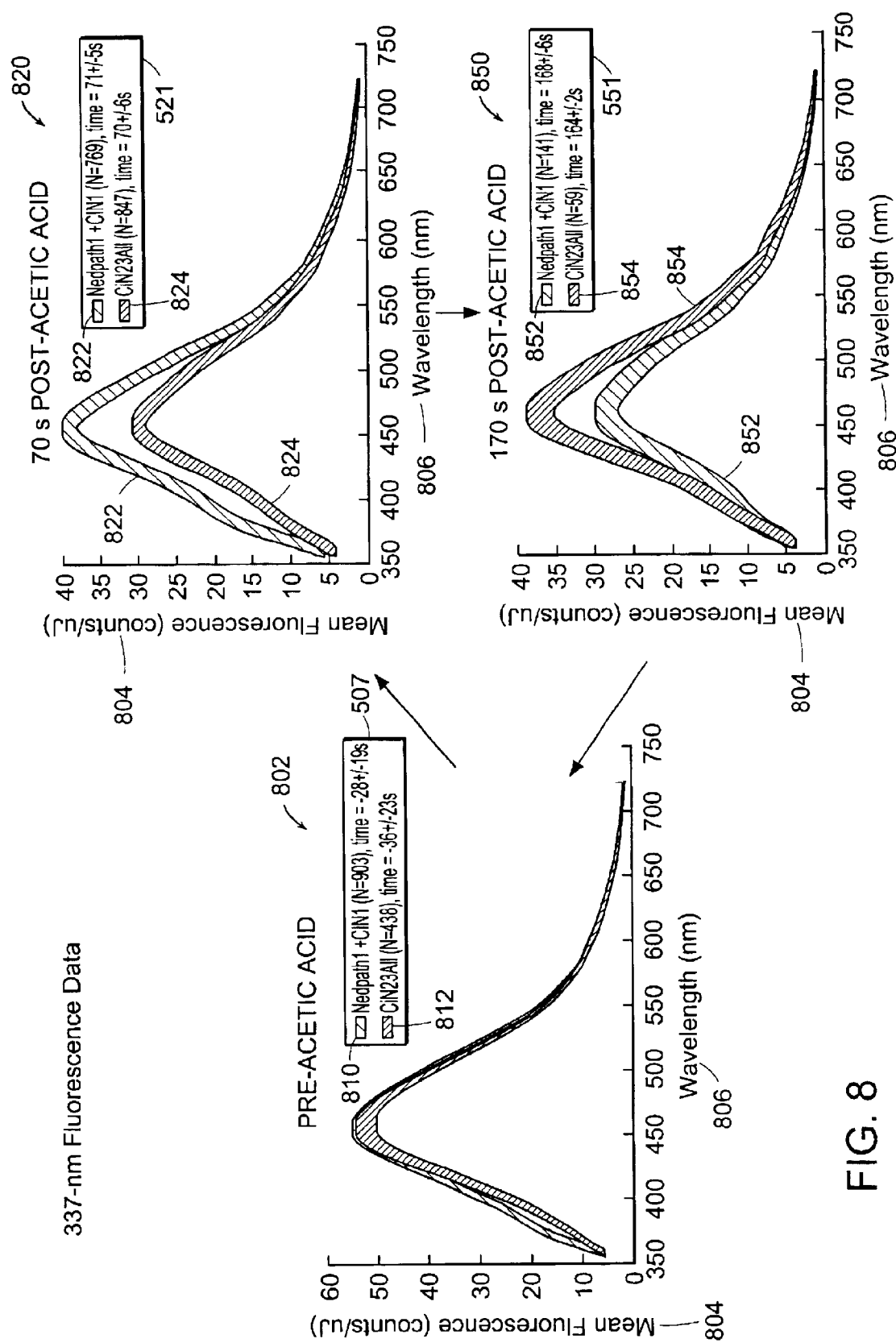
FIG. 8 shows a series of graphs depicting mean fluorescence spectra for CIN 2/3 and non-CIN 2/3 (NED and CIN 1) tissues at a time prior to application of acetic acid, at a time corresponding to maximum whitening, and at a time corresponding to the latest time at which data was obtained.

FIG. 8 shows the difference between the mean 337-nm fluorescence spectra for non-CIN 2/3 tissues (including CIN 1 and NED tissues) and CIN 2/3 tissues at three times—at a time prior to application of acetic acid (graph 802), at a time corresponding to maximum whitening (graph 820, about 60 to about 80 seconds post-AA), and at a time corresponding to the latest time period in which data was obtained (graph 850, about 160 to about 180 seconds post-AA). The time corresponding to maximum whitening was determined from reflectance data, and occurs between about 60 seconds and 80 seconds following application of acetic acid. In the absence of acetic acid, the fluorescence spectra for CIN 2/3 tissue (curve 812 of graph 802 in FIG. 8) and for non-CIN 2/3 tissue (curve 810 of graph 802 in FIG. 8) are essentially equivalent with a slightly lower fluorescence noted around 390 nm for CIN 2/3 sites. Following the application of acetic acid, the fluorescence of CIN 2/3 and non-CIN 2/3 tissues decrease, with CIN 2/3 showing a larger relative percent change (compare curves 824 and 822 of graph 820 in FIG. 8). From about 160 s to about 180 s following acetic acid application, the fluorescence of CIN 2/3 tissue shows signs of returning to the pre-acetic acid state while the fluorescence of the non-CIN 2/3 group continues to decrease (compare curves 854 and 852 of graph 850 in FIG. 8).

Figure 9:
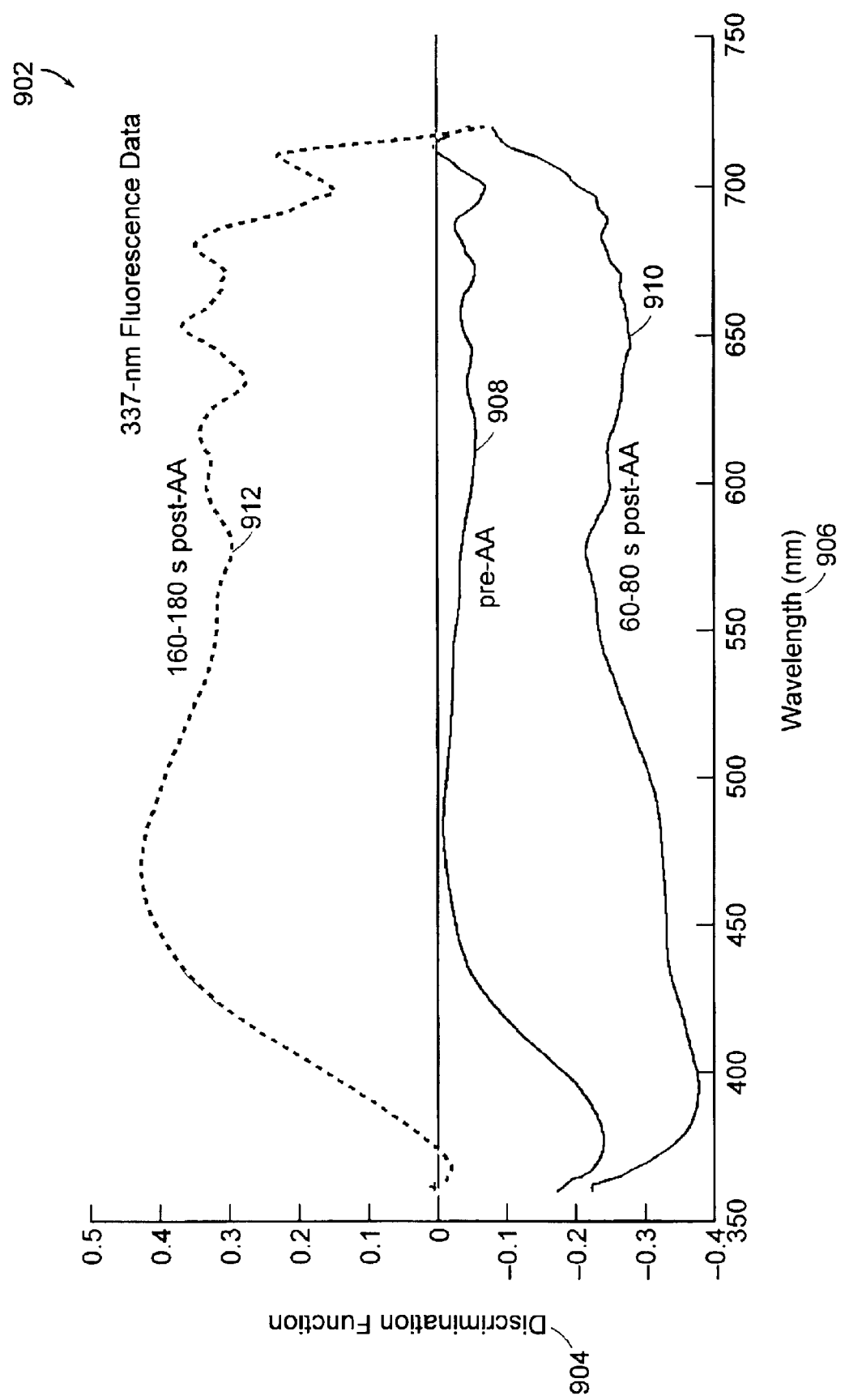
FIG. 9 shows a graph depicting the fluorescence discrimination function spectra useful for differentiating between CIN 2/3 and non-CIN 2/3 (NED and CIN 1) tissues.

In one embodiment, discrimination function 'spectra' are calculated from the fluorescence spectra of CIN 2/3 and non-CIN 2/3 tissues shown in FIG. 8. In one example, discrimination function spectra comprise values of the discrimination function in Equation (1) determined as a function of wavelength for sets of spectral data obtained at various times. FIG. 9 shows a graph 902 depicting the discrimination function spectra evaluated using the fluorescence data of FIG. 8 obtained prior to application of acetic acid, and at two times post-AA. Curve 908 corresponds to the discrimination function 904 evaluated as a function of wavelength 906 using non-CIN 2/3 data and CIN 2/3 data obtained prior to application of acetic acid. Curve 910 corresponds to the discrimination function 904 evaluated as a function of wavelength 906 using non-CIN 2/3 data and CIN 2/3 data obtained between about 60 and about 80 seconds after application of acetic acid; and curve 912 corresponds to the discrimination function 904 evaluated as a function of wavelength 906 using non-CIN 2/3 data and CIN 2/3 data obtained between about 160 and about 180 seconds after application of acetic acid. Distinguishing between CIN 2/3 and non-CIN 2/3 tissues using fluorescence data is improved with the application of acetic acid. Here, the largest absolute values are found from data measured within the range of about 160–180 s post-acetic acid (curve 912), and these agree with the differences seen in the mean fluorescence spectra of FIG. 8 (curves 852 and 854 of graph 850 in FIG. 8).

Performing multivariate linear regression analysis addresses wavelength interdependencies in the development of a classification model. An application of one embodiment comprises classifying data represented in the CIN 2/3, CIN 1, and NED categories in the Appendix Table into CIN 2/3 and non-CIN 2/3 categories by using classification models developed from the fluorescence data shown in FIG. 8. Fluorescence intensities are down-sampled to one about every 10 nm between about 360 and about 720 nm. The model is trained by adding intensities in a forward manner. Testing is performed by a leave-one-spectrum-out jack-knife process. The result of this analysis shows which wavelengths best separate CIN 2/3 from non-CIN 2/3, as shown in Table 3 for an exemplary embodiment.

TABLE 3

Forwarded selected best 337-nm fluorescence wavelengths for classifying CIN 2/3 from non-CIN 2/3 spectra obtained at different times pre and post-AA.

| Time from AA (s) | LDA Model Input Wavelengths (nm) | Accuracy |
|---|---|---|
| -30 | 380, 430, 440, 610, 660, 700, 710 | 61 |
| 30 | 370, 380, 390, 640 | 61 |
| 50 | 410 | 54 |
| 70 | 370, 460, 510, 570, 600, 700, 720 | 76 |
| 90 | 370, 380, 420, 460, 500, 560, 660 | 64 |
| 110 | 360, 390, 400, 710 | 51 |
| 130 | 370 | 53 |
| 150 | 370, 380, 440, 620, 640, 700 | 65 |
| 170 | 370, 480, 510, 570, 600, 700, 720 | 76 |

The two best models for separating CIN 2/3 and non-CIN 2/3 for this embodiment include the method using data obtained at peak CIN 2/3 whitening (60–80 s) and the model using data at the time measured (160–180 s post acetic acid). The first model uses input wavelengths between about 360 and about 670 nm, while the second model uses wavelengths between about 370 and about 720 nm. This is consistent with the discrimination function spectra shown in FIG. 9.

Figure 10:
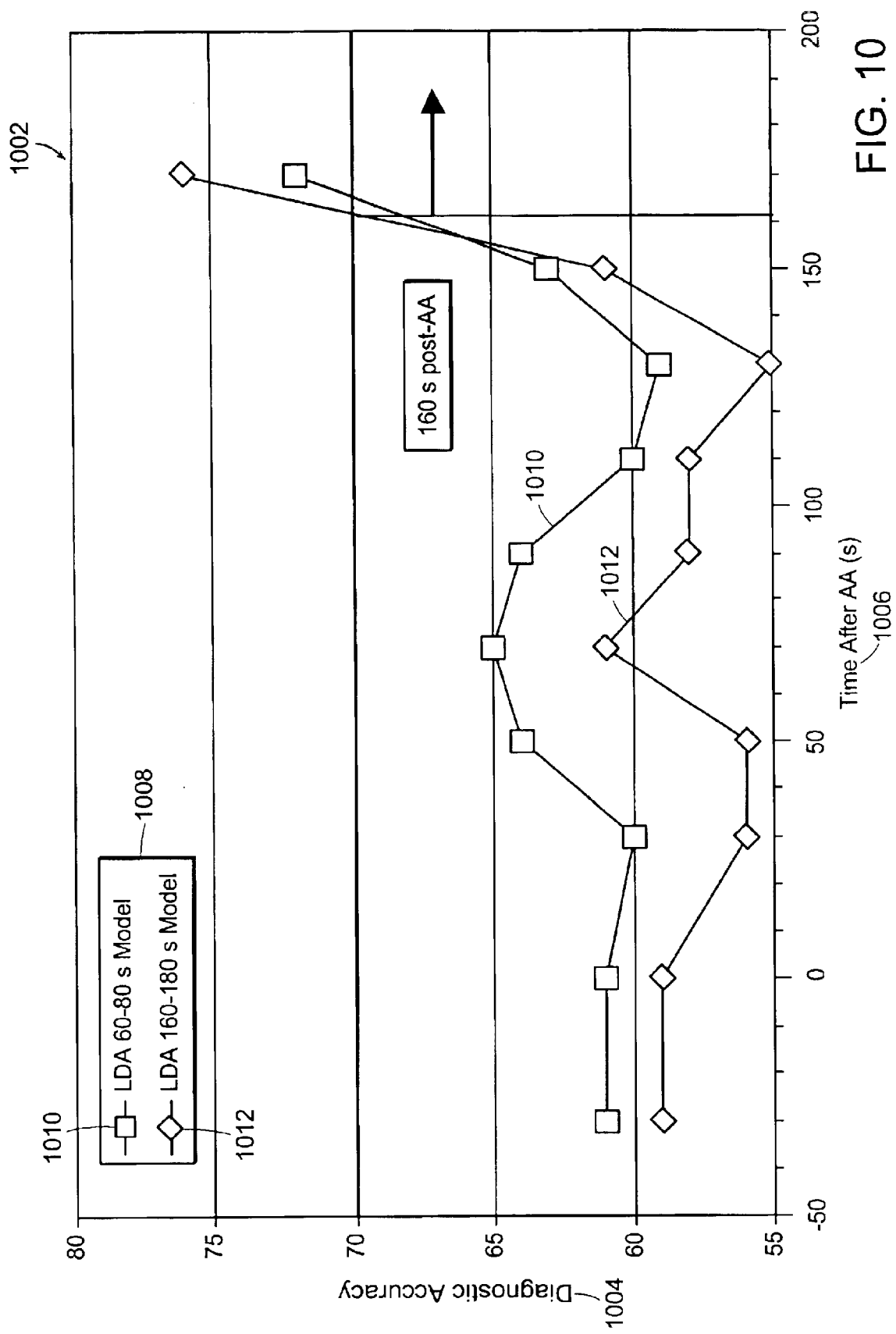
FIG. 10 shows a graph depicting the performance of two LDA (linear discriminant analysis) models as applied to fluorescence data obtained at various times following application of acetic acid; one of the models is based on data obtained between 60 and 80 seconds following application of acetic acid, and the other model is based on data obtained between 160 and 180 seconds following application of acetic acid.

FIG. 10 demonstrates one method of determining an optimal window for obtaining flourescence spectral data in the diagnosis of the state of health of a region of a sample as CIN 2/3 or non-CIN 2/3. FIG. 10 shows a graph 1002 depicting the performance of the two LDA models described in Table 3 above as applied to fluorescence spectral data obtained at various times following application of acetic acid 1006. Curve 1010 in FIG. 10 is a plot of the diagnostic accuracy of the LDA model based on fluorescence spectral data obtained between about 60 and about 80 seconds ("peak whitening model") as applied to fluorescence spectra from the bias of Table 1, and curve 1012 in FIG. 10 is a plot of the diagnostic accuracy of the LDA model based on fluorescence spectral data obtained between about 160 and about 180 seconds, as applied to fluorescence spectra from the bins of Table 1. The accuracies of these models vary depending on when the fluorescence spectra are recorded relative to the application of acetic acid, as shown in FIG. 10. The predictive ability of the fluorescence models in FIG. 10 tend to be less than that of the reflectance models in FIG. 7. Accuracies greater than 70% are obtained with spectra collected after about 160 seconds post-AA.

Another embodiment comprises classifying data represented in the CIN 2/3, CIN 1, and NED categories in the Appendix Table into CIN 2/3 and non-CIN 2/3 categories by using fluorescence divided by diffuse reflectance spectra. Models are developed based on time post acetic acid. Ratios of fluorescence to reflectance are down-sampled to one every 10 nm between about 360 and about 720 nm. The model is trained by adding intensities in a forward manner. Testing is performed by a leave-one-spectrum-out jack-knife process. For this analysis, the model is based on intensities at about 360, 400, 420, 430, 560, 610, and 630 nm. In general, the results are slightly better than a model based on fluorescence alone. Improved performance is noted from spectra acquired at about 160 s post acetic acid.

Figure 11:
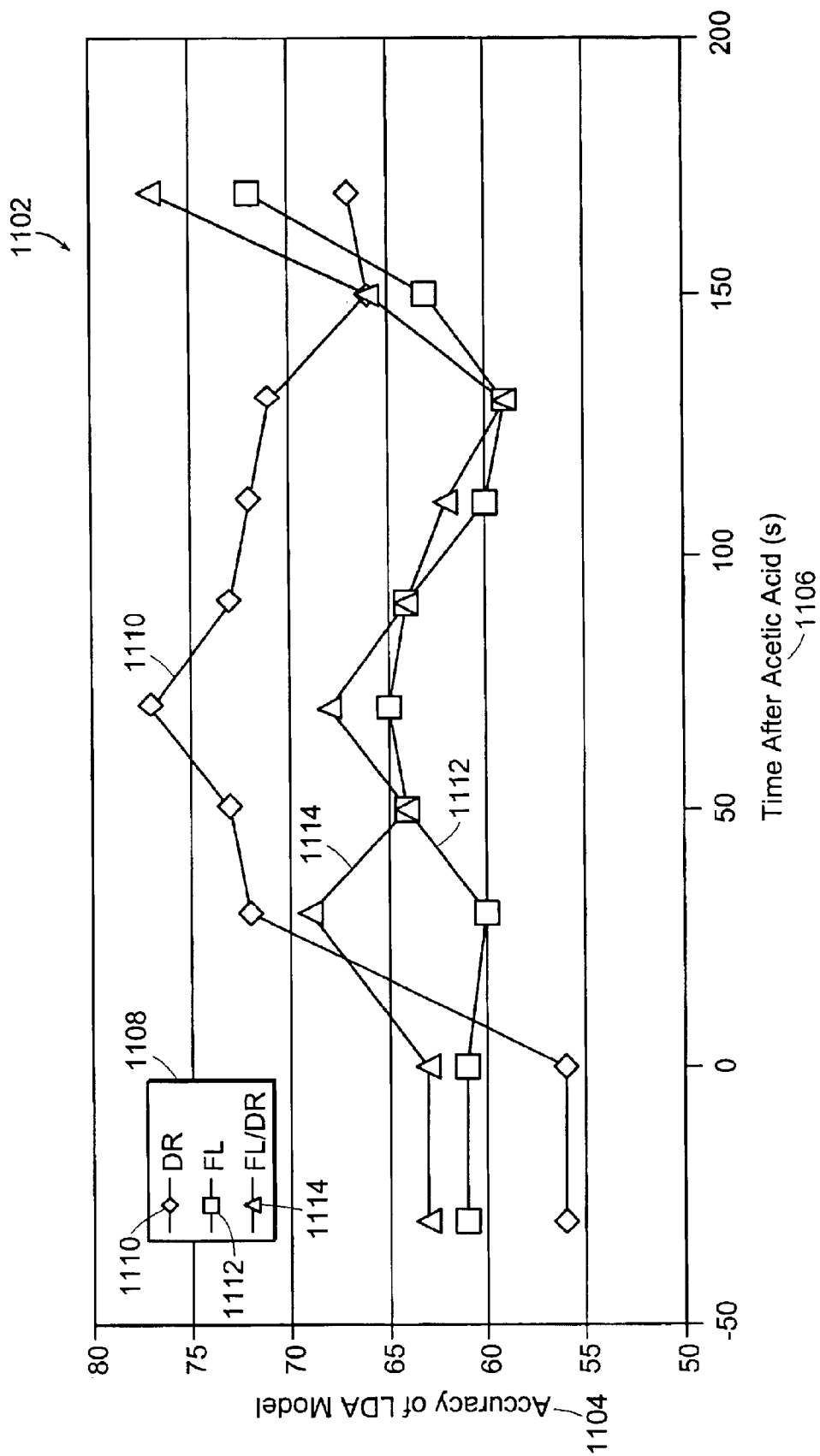
FIG. 11 shows a graph depicting the performance of three LDA models as applied to data obtained at various times following application of acetic acid.

FIG. 11 shows a graph 1102 depicting the accuracy of three LDA models as applied to spectral data obtained at various times following application of acetic acid. Curve 1110 in FIG. 11 is a plot of the diagnostic accuracy of the LDA model based on reflectance spectral data obtained between about 60 and about 80 seconds ("peak whitening model"), also shown as curve 710 in FIG. 7. Curve 1112 in FIG. 11 is a plot of the diagnostic accuracy of the LDA model based on fluorescence spectral data obtained between about 60 and about 80 seconds ("peak whitening model"), also shown as curve 1010 in FIG. 10. Curve 1114 in FIG. 11 is a plot of the diagnostic accuracy of the LDA model based on fluorescence intensity divided by reflectance, as described in the immediately preceding paragraph.

The exemplary embodiments discussed above demonstrate that the ability to distinguish between non-CIN 2/3 and CIN 2/3 fluorescence and reflectance spectra is improved with the application of acetic acid or other contrast agent. For the peak-whitening LDA model using reflectance data, the highest accuracy for the exemplary applications of the embodiments discussed herein is obtained at about 70 s following introduction of acetic acid, while accuracies greater than about 70% are obtained with spectra collected in a window between about 30 s and about 130 s. The predictive ability of the fluorescence models in the examples above tend to be less than that of the reflectance models for the examples discussd above. Accuracies greater than 70% are obtained with fluorescence at times greater than about 160 s post acetic acid. The intensity of fluorescence continuously drop over the measurement period in the non-CIN groups while partial recovery occurs at all 3 emission wavelengths in the CIN 2/3 group, suggesting that fluorescence spectral data obtained at times greater than about 180 s is useful in diagnosing CIN 2/3.

EXAMPLE 4

Other Kinetics-based Approaches for Obtaining Diagnostic Optical Data Within an Optimal Window.

As an alternative to the techniques discussed above, other kinetics-based approaches may be used to determine classification models and, hence, corresponding optimum windows for classification of tissue samples. The time response of fluorescence intensity or the time response of reflectance following application of contrast agent, as shown in FIG. 3 and FIG. 4, may be curve-fitted to determine one or more parameters sensitive to a curve feature of interest. For example, a parameter sensitive to a local minimum may be determined for a given set of fluorescence response data. In one embodiment, a parameter is determined by curve-fitting fluorescence time response data to a sigmoidal function. Values of the parameter and/or goodness-of-fit data are then used to develop a statistical model for classifying a sample in terms of a characteristic of the sample, such as its state of health. The model is built using reference data with known states of health. Then, the time response of spectral intensity of a test sample with unknown state of health following application of a contrast agent is obtained. By curve-fitting this response data, values of the indicated parameter(s) may be obtained, and the model may be used to either directly determine the characteristic of the test sample, or to indicate an optimal window in which spectral data should be obtained and used to accurately classify the tissue. In one embodiment, the parameter determined by curve-fitting spectral time response curves is not used directly to classify the tissue, but is used to determine an optimal window. The parameter indicates a window of time in which one or more complete sets of spectral and/or video data should be obtained for accurate diagnosis of the tissue.

EXAMPLE 5

Using a Relative Change or Rate-of-change Trigger to Obtain Diagnostic Optical Data An embodiment of the invention comprises determining and using a relative amplitude change and/or rate of amplitude change as a trigger for obtaining diagnostic optical data from a sample. The trigger can also be used to determine an optical window of time for obtaining such diagnostic optical data. By using statistical and/or heuristic methods such as those discussed herein, it is possible to relate more easily-monitored relative changes or rates-of-change of one or more optical signals from a tissue sample to corresponding full spectrum signals that can be used in characterizing the state of health of a given sample. For example, by performing a discrimination function analysis, it may be found for a given tissue type that when the relative change in reflectance at a particular wavelength exceeds a threshold value, the corresponding full-spectrum reflectance can be obtained and then used to accurately classify the state of health of the tissue. In addition, the triggers determined above may be converted into optimal time windows for obtaining diagnostic optical data from a sample.

Figure 12A:
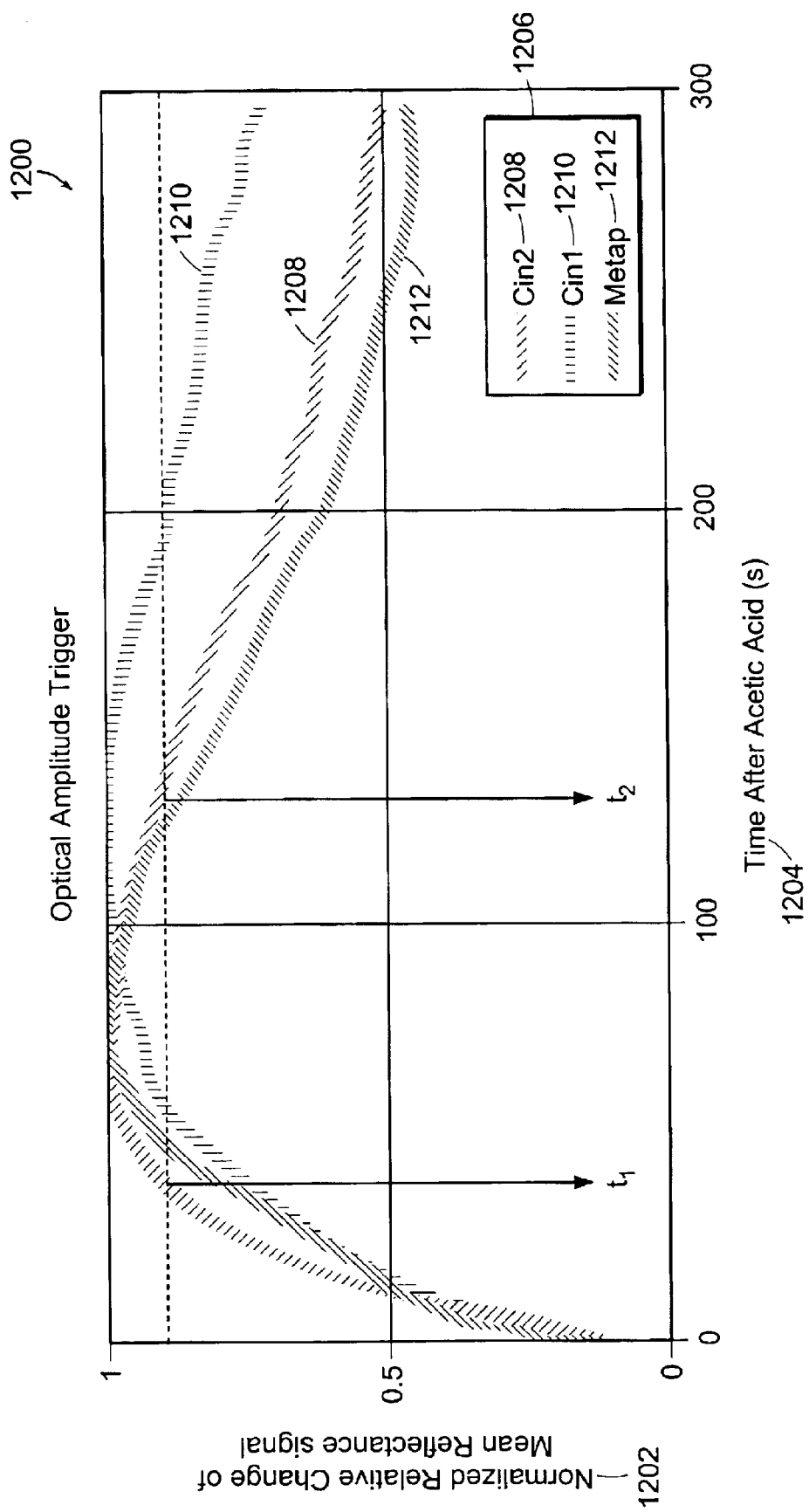
FIG. 12A shows a graph depicting the determination of an optimal time window for obtaining diagnostic optical data using an optical amplitude trigger.

FIG. 12A shows how an optical amplitude trigger can be used to determine an optimal time window for obtaining diagnostic optical data. The graph 1200 in FIG. 12A plots the normalized relative change of mean reflectance signal 1202 from tissue samples with a given state of health as a function of time following application of acetic acid 1204. The mean reflectance signal determined from CIN 1, CIN 2, and Metaplasia samples are depicted in FIG. 12A by curves 1210, 1208, and 1212, respectively. Here, it was determined that when the normalized relative change of mean reflectance reaches or exceeds 0.75, the image intensity data and/or the full reflectance and/or fluorescence spectrum for a given sample is most indicative of a given state of health of a sample. Thus, for CIN 2 samples, for example, this corresponds to a time period between $t_1$ and $t_2$, as shown in the graph 1200 of FIG. 12A. Therefore, spectral and/or image data obtained from a tissue sample between $t_1$ and $t_2$ seconds following application of acetic acid can be used in accurately determining whether or not CIN 2 is indicated for that sample. In one embodiment, the relative change of reflectance of a tissue sample at one or more given wavelengths is monitored, and when that relative change is greater than or equal to the 0.75 threshold, more comprehensive spectral and/or image data is obtained from the sample for purposes of characterizing whether or not the sample is indicative of CIN 2. FIG. 12A demonstrates the use of a threshold value of relative optical signal change. In another embodiment, a predetermined range of values of the relative optical signal change is used such that when the relative signal change falls within the predetermined range of values, additional spectral and/or image data is captured in order to characterize the sample.

Figure 12B:
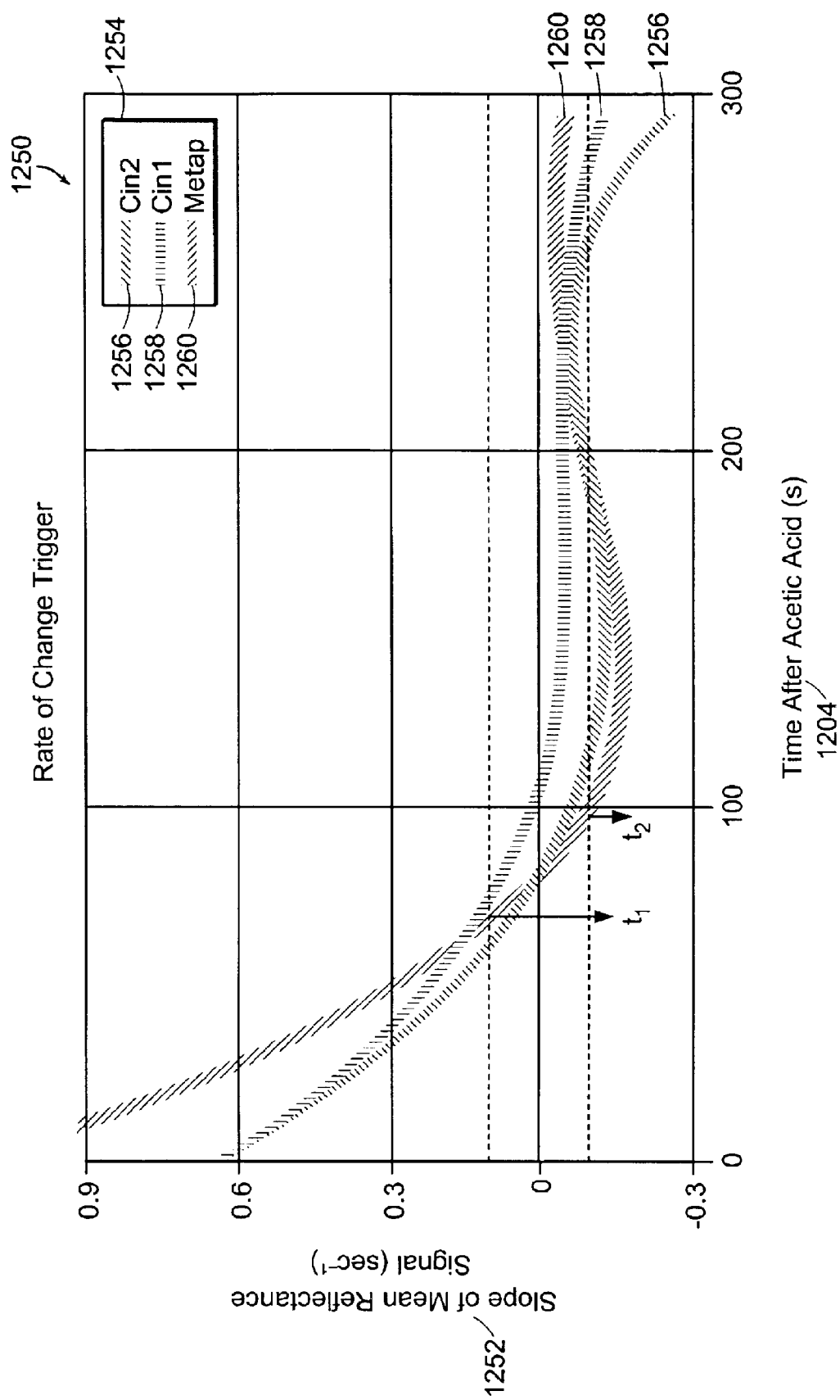
FIG. 12B shows a graph depicting the determination of an optimal time window for obtaining diagnostic data using a rate of change of mean reflectance signal trigger.

FIG. 12B shows how a rate-of-change of optical amplitude trigger can be used to determine an optimal time window for obtaining diagnostic optical data. The graph 1250 of FIG. 12B plots the slope of mean reflectance signal 1252 from tissue samples with a given state of health as a function of time following application of acetic acid 1204. The slope of mean reflectance is a measure of the rate of change of the mean reflectance signal. The rate of change of mean reflectance determined from CIN 1, CIN 2, and Metaplasia samples are depicted in FIG. 12B by curves 1258, 1256, and 1260, respectively. Here, it was determined that when the absolute value of the slope has an absolute value less than or equal to 0.1, for example, in the vicinity of maximum reflectance, the image intensity data and/or the full reflectance and/or fluorescence spectrum for a given sample is most indicative of a given state of health of a sample. Thus, for CIN 2 samples, for example, this corresponds to a time period between $t_1$ and $t_2$ as shown in the graph 1250 of FIG. 12B. Therefore, spectral and/or image data obtained from a tissue sample between $t_1$ and $t_2$ seconds following application of acetic acid can be used in accurately determining whether or not CIN 2 is indicated for that sample. In one embodiment, the rate of change of reflectance of a tissue sample is monitored at one or more given wavelengths, and when that rate of change has an absolute value less than or equal to 0.1, more comprehensive spectral and/or image data is obtained from the sample for purposes of characterizing whether or not the sample is indicative of CIN 2. FIG. 12B demonstrates use of a range of values of rate of optical signal change. Other embodiments use a single threshold value.

EXAMPLE 6

Using Fluorescence, Reflectance and/or Image Time Response Data to Diagnose Regions of Tissue The figures discussed herein include time-response fluorescence and reflectance data obtained following application of a contrast agent to tissue. In addition to an acetowhitening effect observed in the reflectance data, an "acetodarkening" effect is observed in the fluorescence data. For example, the fluorescence intensity of diseased regions decreases to a minimum at about 70 s to about 130 s following application of acetic acid. Thus, the presence of a minimum fluorescence intensity within this window of time, as well as the accompanying increase in fluorescence from this minimum, may be used to indicate disease. An embodiment of the invention comprises a method of identifying a characteristic of a region of a tissue sample including applying a contrast agent to a region of a tissue sample, obtaining at least two values of fluorescence spectral intensity corresponding to the region, determining whether the fluorescence spectral intensity corresponding to the region increases after a predetermined time following the applying step, and identifying a characteristic of the region based at least in part on the determining step. In an embodiment, the obtaining step comprises obtaining a fluorescence spectral intensity signal corresponding to the region as a function of time following the applying step. In an embodiment, the method further comprises determining whether the fluorescence spectral intensity corresponding to the region decreases following the applying step, then increases after the predetermined time. In an embodiment, the predetermined time is about 80 seconds.

An embodiment comprises a method of identifying a characteristic of a region of a tissue sample comprising applying a contrast agent to a region of a tissue sample, obtaining a fluorescence spectral intensity signal from the region of the tissue sample, determining an elapsed time following the applying step at which the fluorescence spectral intensity signal has a minimum value, and identifying a characteristic of the region based at least in part on the elapsed time.

An embodiment comprises a method of identifying a characteristic of a region of a tissue sample comprising applying a contrast agent to a region of a tissue sample, obtaining a reflectance signal from the region of the tissue sample, determining a change in reflectance spectral intensity corresponding to the region of the tissue sample following the applying step, and identifying a characteristic of the region based at least in part on the change in reflectance spectral intensity. In an embodiment, the change in reflectance spectral intensity corresponding to the region comprises a change relative to an initial condition of the region.

An embodiment comprises a method of identifying a characteristic of a region of a tissue sample comprising applying a contrast agent to a region of a tissue sample, obtaining an optical signal from the region of the tissue sample, determining a rate of change of the optical signal corresponding to the region of the tissue sample, and identifying a characteristic of the region based at least in part on the rate of change. In an embodiment, the optical signal comprises fluorescence spectral intensity at a given wavelength. In an embodiment, the optical signal comprises reflectance spectral intensity at a given wavelength.

An embodiment comprises a method of identifying a characteristic of a region of a tissue sample comprising applying a contrast agent to a region of a tissue sample, obtaining a fluorescence signal from the region of the tissue sample, obtaining a reflectance signal from the region of the tissue sample, and identifying a characteristic of the region based at least in part on the fluorescence signal and the reflectance signal.

An embodiment comprises obtaining an optical signal from 499 regions, each region having a diameter of approximately 1 mm, covering an area of tissue about 25 mm in diameter. An embodiment may also comprise obtaining a video image of about 480 by about 560 pixels covering the same 25-mm diameter area of tissue.

APPENDIX TABLE

Number of spectra (number of subject) for each tissue class in each time bin for exemplary embodiments discussed herein.

| Time | CIN 2/3 | CIN 1 | Metaplasia | TT_022[1] | TT_025[1] | NEDpath1[1] |
|---|---|---|---|---|---|---|
| $t \leq 0$ | 451 (62) | 202 (46) | 329 (77) | 202 (56) | 294 (70) | 816 (186) |
| $0 < t \leq 40$ | 118 (21) | 72 (14) | 147 (33) | 51 (14) | 113 (22) | 307 (64) |
| $40 < t \leq 60$ | 300 (47) | 135 (31) | 255 (58) | 116 (32) | 230 (51) | 597 (133) |
| $60 < t \leq 80$ | 375 (54) | 162 (39) | 300 (68) | 179 (42) | 262 (61) | 731 (157) |
| $80 < t \leq 100$ | 455 (60) | 195 (42) | 308 (70) | 190 (49) | 263 (64) | 752 (167) |
| $100 < t \leq 120$ | 446 (60) | 209 (45) | 328 (76) | 208 (52) | 284 (68) | 811 (178) |
| $120 < t \leq 140$ | 303 (44) | 135 (30) | 200 (48) | 165 (43) | 185 (51) | 545 (129) |
| $140 < t \leq 160$ | 130 (18) | 82 (17) | 75 (19) | 96 (23) | 66 (21) | 232 (53) |
| $160 < t \leq 180$ | 53 (9) | 50 (9) | 34 (9) | 38 (12) | 19 (6) | 91 (24) |
| $t > 180$ | 14 (3) | 26 (3) | 33 (6) | 23 (6) | 30 (5) | 86 (15) |

[1]TT_022 = Normal columnar tissue; TT_025 = Normal squamous tissue; NEDPath1 = NED = Metaplasia, TT_022, and TT_025.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of identifying a characteristic of a region of a tissue sample, the method comprising the steps of:
   (a) applying a contrast agent comprising acetic acid to a region of a tissue sample;
   (b) obtaining at least one optical signal from the region within a window of time, wherein the window of time begins at about 30 seconds following application of the contrast agent and ends at about 130 seconds following application of the contrast agent, and wherein the at least one optical signal comprises at least one of:
      (i) a fluorescence signal; and
      (ii) a reflectance signal; and
   (c) identifying a characteristic of the region based at least in part on the at least one optical signal.

2. The method of claim 1, wherein the at least one optical signal comprise a reflectance intensity.

3. The method of claim 1, wherein the at least one optical signal comprise a fluorescence intensity.

4. The method of claim 1, wherein the at least one optical signal comprises at least one of a group consisting of fluorescence, reflectance, Raman, infrared, and video signals.

5. The method of claim 1, wherein the characteristic is a state of health.

6. The method of claim 5, wherein the state of health comprises at least one of the group consisting of normal squamous tissue, normal columnar tissue, metaplasia, immature metaplasia, mature metaplasia, CIN 1, CIN 2, CIN 3, CIS, and cancer.

7. The method of claim 1, wherein the identifying of step (c) comprise determining whether the region of the tissue sample is CIN 2+ tissue.

8. The method of claim 1, wherein the tissue sample comprises cervical tissue.

9. The method of claim 1, wherein the tissue sample comprises at least one of a group consisting of colorectal tissue, gastroesophageal tissue, urinary bladder tissue, lung tissue, and skin tissue.

10. The method of claim 1, wherein the tissue sample comprises epithelial cells.

11. The method of claim 1, wherein the at least one optical signal comprises a fluorescence signal and a reflectance signal.

12. The method of claim 1, wherein the at least one optical signal comprise two reflectance signals.

13. The method of claim 1, wherein the at least one optical signal comprise a fluorescence signal and two reflectance signals.

14. The method of claim 1, wherein the at least one optical signal comprise a fluorescence signal, a reflectance signal, and a video signal.

15. The method of claim 1, wherein step (b) comprises obtaining the at least one optical signal from the region within a period-of time that begins at about 60 seconds following application of the contrast agent and ends at about 80 seconds following application of the contrast agent.

16. The method of claim 1, wherein step (b) comprises obtaining the at least one optical signal from the region within a period of time that begins at about 70 seconds following application of the contrast agent and ends at about 130 seconds following application of the contrast agent.

17. The method of claim 1, wherein step (c) comprises identifying the characteristic of the region with an accuracy of at least about 70%.

18. The method of claim 1, wherein step (b) comprises obtaining a reflectance intensity from the region at each of a plurality of wavelengths within the window of time.

19. The method of claim 18, wherein step (b) further comprises obtaining a fluorescence intensity from the region at each of a plurality of wavelengths within the window of time.

20. The method of claim 19, wherein step (b) further comprises obtaining a video signal from the region within the window of time.

21. The method of claim 1, wherein step (a) comprises applying a contrast agent to a plurality of regions of the tissue sample; step (b) comprises obtaining at least one optical signal from each of the plurality of regions within the window of time; and step c) comprises identifying a characteristic of each of the plurality of regions.

22. The method of claim 1, wherein step (c) comprises identifying the characteristic of the region based substantially on the at least one optical signal.

23. The method of claim 1, wherein the contrast agent comprises an acetic acid solution at a concentration between about 3 volume percent and about 6 volume percent.

24. The method of claim 23, wherein the contrast agent comprises an acetic acid solution at a concentration of about 5 volume percent.

* * * * *